US006866461B2

(12) United States Patent
DeWinter et al.

(10) Patent No.: US 6,866,461 B2
(45) Date of Patent: Mar. 15, 2005

(54) DEVICE AND METHODS FOR AUTOMATING TRANSFER OF MULTIPLE SAMPLES TO AN ANALYTICAL INSTRUMENT

(75) Inventors: Scott M. DeWinter, Oakland, CA (US); John B. Rusconi, Dublin, CA (US); Steven M. Clark, Palo Alto, CA (US); Michael P. Lucas, Milpitas, CA (US); Michael G. Youngquist, Palo Alto, CA (US)

(73) Assignee: Ciphergen Biosystems, Inc., Fremont, CA (US)

( * ) Notice: Subject to any disclaimer, the term of this patent is extended or adjusted under 35 U.S.C. 154(b) by 191 days.

(21) Appl. No.: 10/375,507

(22) Filed: Feb. 25, 2003

(65) Prior Publication Data

US 2003/0180128 A1 Sep. 25, 2003

Related U.S. Application Data

(60) Provisional application No. 60/359,940, filed on Feb. 26, 2002, and provisional application No. 60/374,889, filed on Apr. 23, 2002.

(51) Int. Cl.[7] .............................................. B65G 65/00
(52) U.S. Cl. .................................... 414/222.07; 422/63
(58) Field of Search .......................... 414/222.07, 403, 414/416.01; 422/50, 63; 324/321; 250/491.1

(56) References Cited

U.S. PATENT DOCUMENTS

| | | |
|---|---|---|
| 4,076,982 A | 2/1978 | Ritter et al. |
| 4,405,860 A | 9/1983 | Brunnee et al. |
| 4,634,865 A | 1/1987 | Conway |
| 4,879,458 A | 11/1989 | Brunfeldt et al. |
| 5,041,266 A | 8/1991 | Fox |

(List continued on next page.)

FOREIGN PATENT DOCUMENTS

GB 2312782 5/1997

OTHER PUBLICATIONS

Amersham Biosciences, "Amersham Biosciences—Products—EttanTM MALDI–ToF Pro", http://www.amershambiosciences.com/stiboasp/showmodule.asp?nModuleid=164353.
Amersham Biosciences, "Automate Your protein identification with Ettan MALDI–ToF Pro", 2002.
Corning Life Sciences Catalog, "Microplate StackAttacker", http://catalog.corning.com/Lifesciences/us–canada/en/product.asp?catalog%5Fname=Lifesciences&Application=0&ProductCatalogCategory=Microplates+%2DFamily&category%5Fname=Microplate+StackAttacker+%2DClass&product%5Fid=X5034&Region=na&Language=en.

*Primary Examiner*—Donald W. Underwood
(74) *Attorney, Agent, or Firm*—Fish & Neave LLP; James F. Haley; Chi-Hsin Chang

(57) ABSTRACT

The present invention comprises a loading device for automating transfer of a plurality of probes between a cassette within which the plurality of probes are initially constrained and an analytical instrument, e.g., mass spectrometer. The loading device may be configured to accept a single or a plurality of cassettes each removably constraining a plurality of probes to be analyzed. The loading device may permit each of the plurality of cassettes to be independently interchanged with a separate cassette removably constraining a separate plurality of probes during mass spectrometric analysis, or for additional cassettes to be loaded into the device during analysis. In a useful embodiment, the loading device comprises a cassette transport assembly and a probe insertion assembly. The cassette transport assembly linearly translates one or more cassettes to align the cassette(s) with respect to the mass spectrometer so that a probe may be translated therebetween by the probe insertion assembly. The probe insertion assembly also provides means to rotatably engage said probe.

68 Claims, 29 Drawing Sheets

U.S. PATENT DOCUMENTS

| | | |
|---|---|---|
| 5,288,644 A | 2/1994 | Beavis et al. |
| 5,453,702 A | 9/1995 | Creeden |
| 5,498,545 A | 3/1996 | Vestal |
| 5,705,814 A | 1/1998 | Young et al. |
| 5,818,246 A | 10/1998 | Zhong |
| 6,093,930 A | 7/2000 | Boyette, Jr. et al. |
| 6,268,131 B1 | 7/2001 | Kang et al. |
| RE37,485 E | 12/2001 | Vestal |
| 6,458,324 B1 * | 10/2002 | Schinzel .................. 422/63 X |
| 6,555,813 B1 | 4/2003 | Beecher et al. |

* cited by examiner

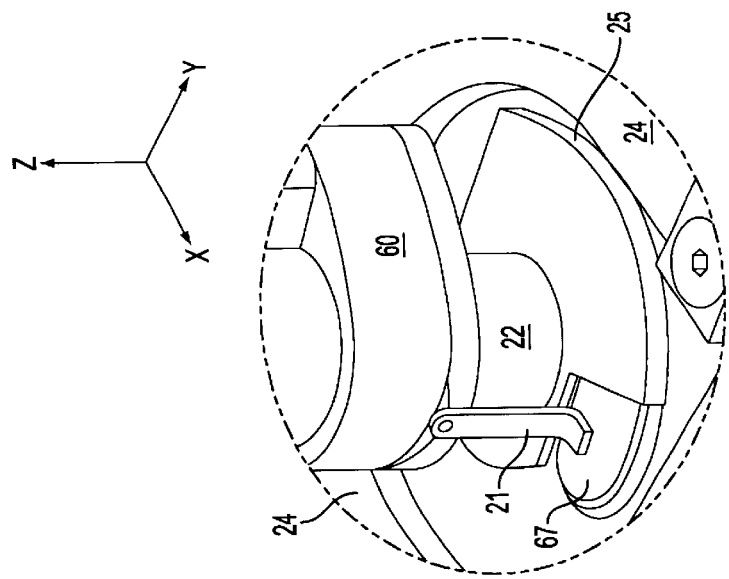
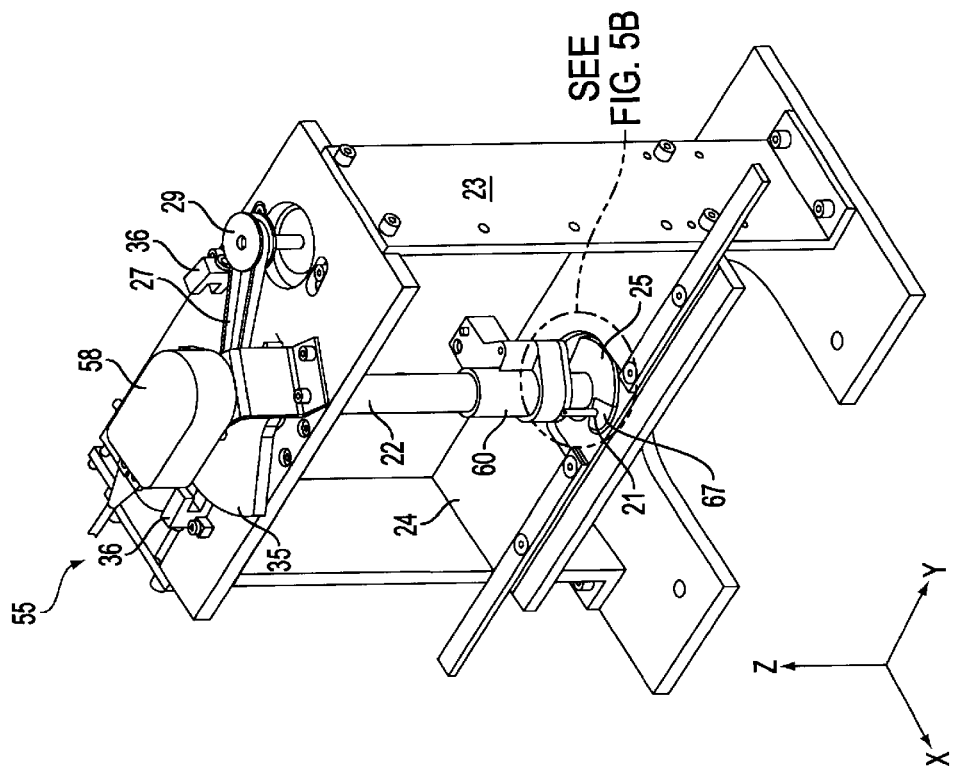
FIG. 5B
FIG. 5A

SECTION AA-AA

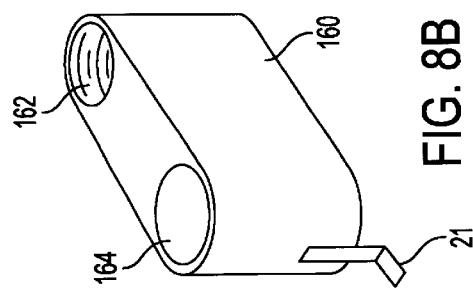
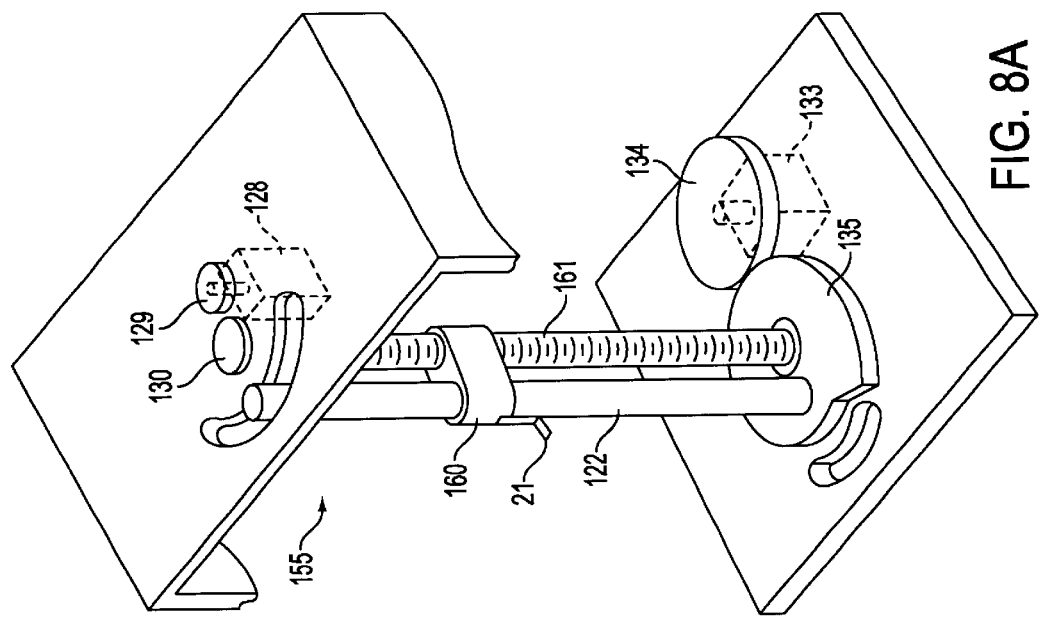

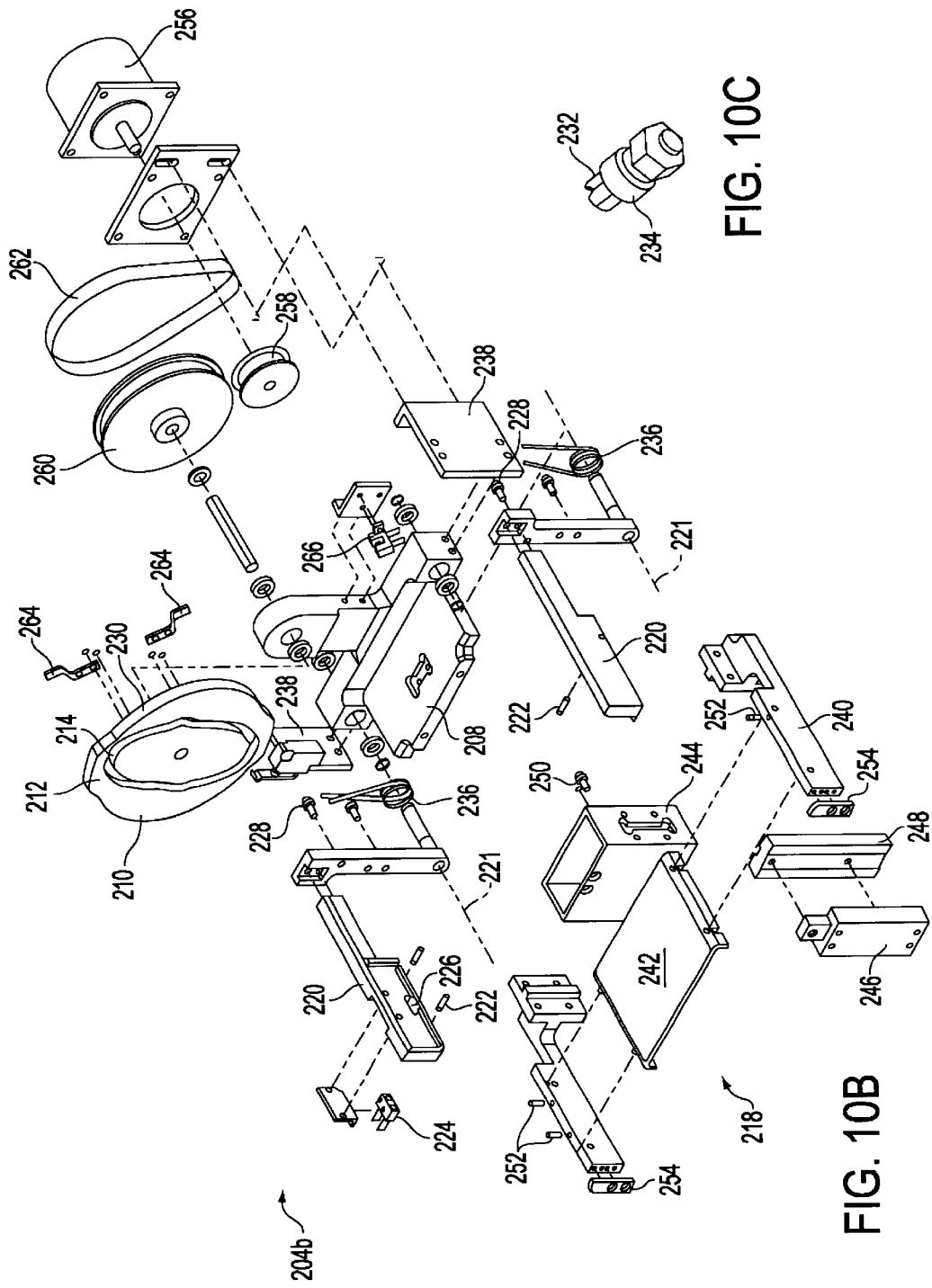

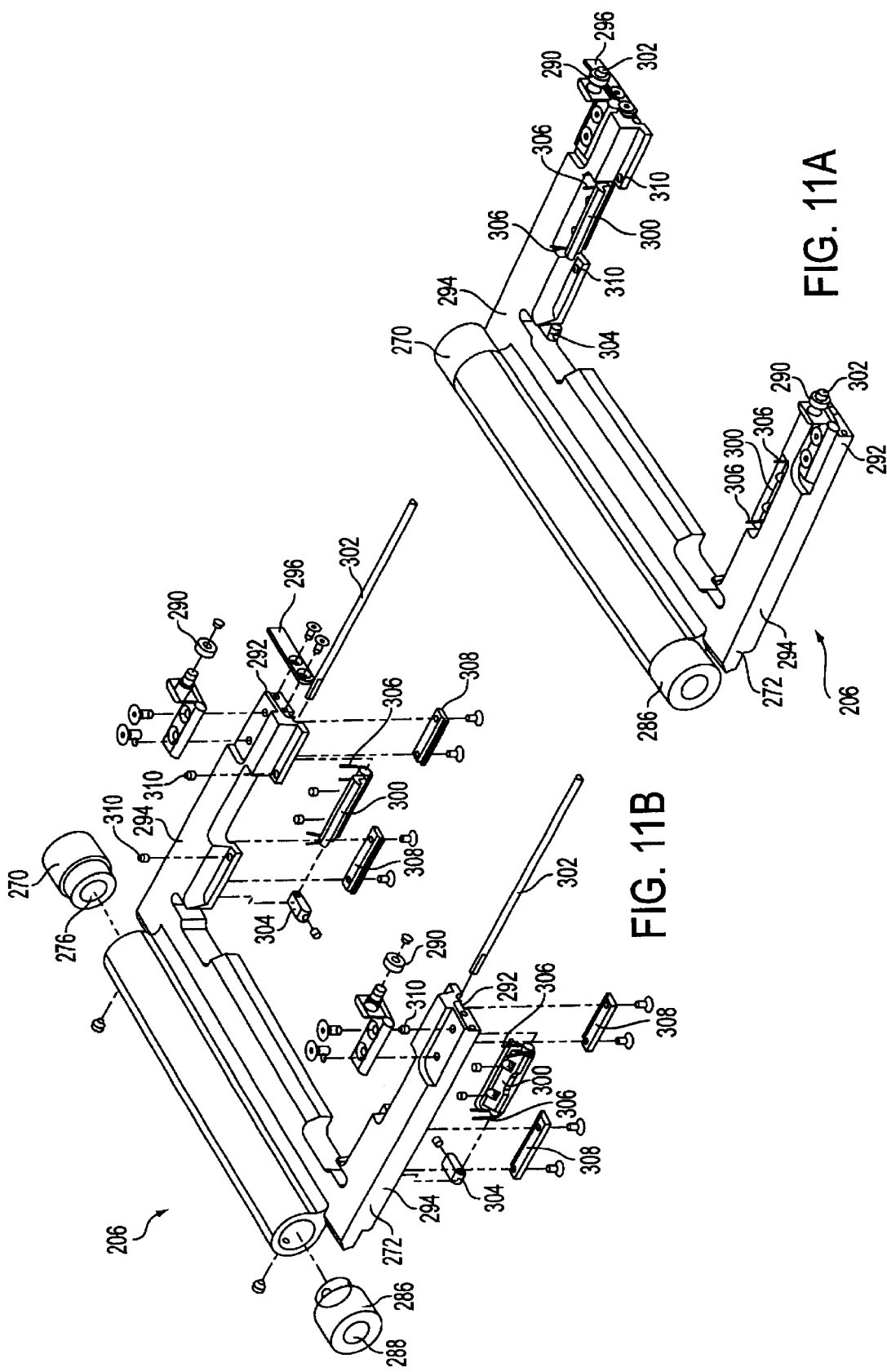

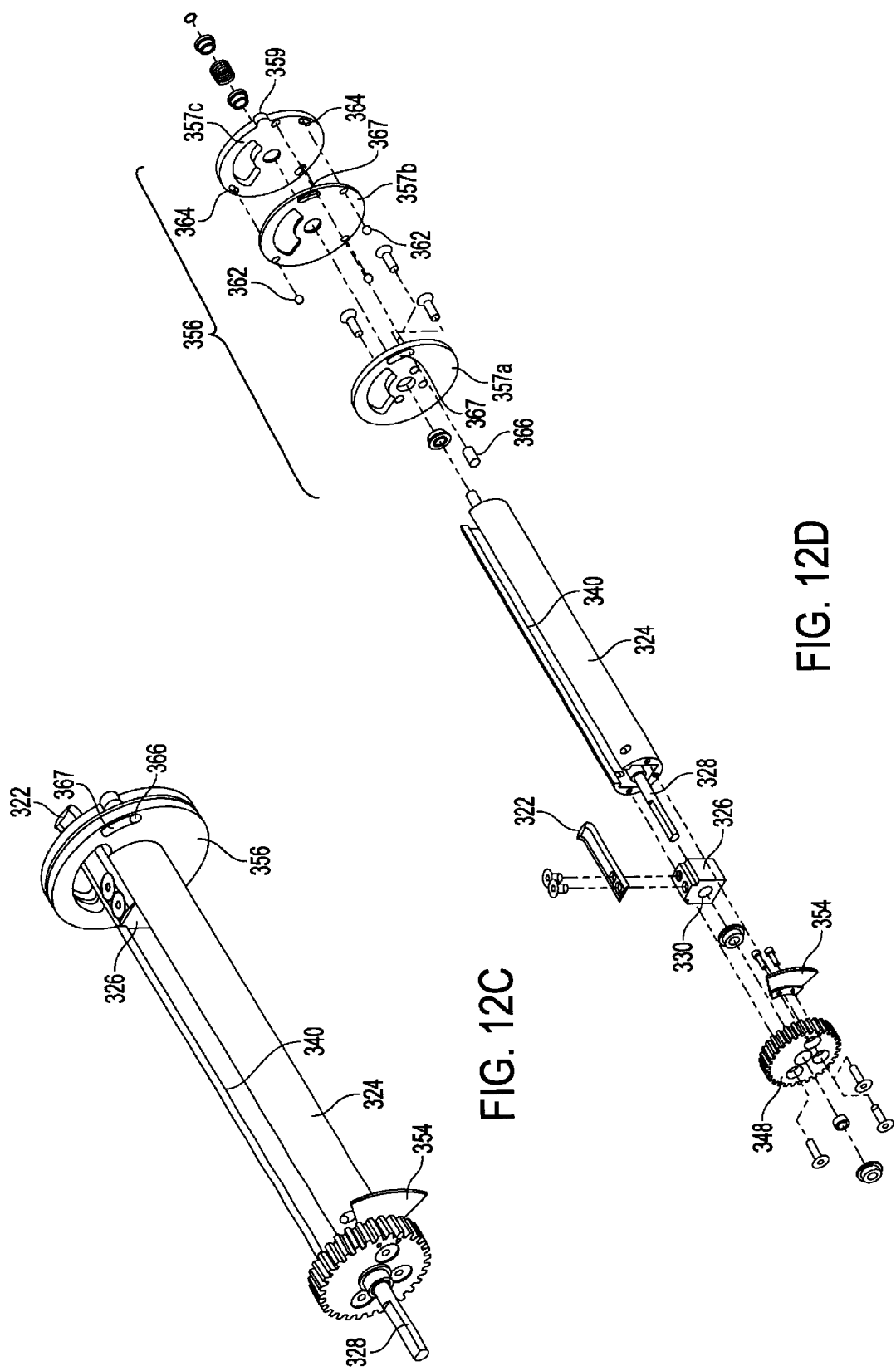

DEVICE AND METHODS FOR AUTOMATING TRANSFER OF MULTIPLE SAMPLES TO AN ANALYTICAL INSTRUMENT

CROSS-REFERENCE TO RELATED APPLICATIONS

This application claims priority to U.S. provisional patent application Ser. No. 60/359,940, filed Feb. 26, 2002, and U.S. provisional patent application Ser. No. 60/374,889, filed Apr. 23, 2002, the disclosures of which are incorporated by reference in their entireties.

FIELD OF THE INVENTION

The present invention relates to a system and methods for automating transfer of multiple samples to an analytical instrument. Particularly, the present invention embodies a system and methods in which multiple sample probes, upon or within which the samples are deposited or disposed, are transferred between a cassette within which the plurality of probes are initially constrained and the analytical instrument.

BACKGROUND OF THE INVENTION

Over the past decade, improvements in mass spectrometry (MS) have allowed MS to take a place among standard analytical tools in the study of biologically relevant macromolecules, notably proteins purified from complex biological systems. For example, the development of matrix-assisted laser desorption/ionization approaches has permitted MS analysis to be applied to large molecular weight analytes, including proteins as large as several hundred kilodaltons, while affinity capture laser desorption/ionization approaches have made possible the selective concentration from inhomogeneous samples of desired analytes directly on active surfaces of the sample probes. Improvements in hardware, including control and detection electronics, have led to improved sensitivity, mass accuracy and resolution, while improved software algorithms have improved the ability to use the data so obtained to identify unknown analytes.

In affinity capture laser desorption/ionization, the active surfaces of the laser desorption/ionization probe are affinity capture surfaces, which are capable of adsorbing analytes selectively from heterogeneous samples, concentrating them on the probe surface in a form suitable for subsequent laser desorption/ionization. The probes then are used to deliver the samples into a mass spectrometer for interrogation by a laser source. Optionally, energy-absorbing (or "matrix") molecules are applied prior to analysis.

Affinity capture surfaces of affinity capture laser desorption/ionization probes can include either a chromatographic or a biomolecule affinity moiety. Chromatographic affinity surfaces have an adsorbent capable of chromatographic discrimination among or separation of analytes. Such surfaces can thus include anion exchange moieties, cation exchange moieties, reverse phase moieties, metal affinity capture moieties, and mixed-mode adsorbents, as such terms are understood in the chromatographic arts. Biomolecule affinity surfaces have an adsorbent comprising biomolecules capable of specific binding. Such surfaces can thus include antibodies, receptors, nucleic acids, lectins, enzymes, biotin, avidin, streptavidin, Staph protein A and Staph protein G.

Liquid samples typically applied to the active surfaces of laser desorption/ionization probes, including affinity capture laser desorption/ionization probes, are typically several microliters in volume; after subsequent purification processes, usually only picomoles to nanomoles of analytes remain for analysis in the mass spectrometer.

With such small quantities of analytes, and with spectrometers having such high sensitivity, contamination of the active surfaces is a major problem in use of probes. Specifically, when an operator handles and transfers the probes, there are numerous opportunities for the operator inadvertently to grasp the probes on or near one or more of its active surfaces (such as affinity capture surfaces)—and consequently, to contaminate the samples thereon with finger proteins, such as collagen, and dirt. For example, an operator is presently called upon to handle each probe at least three times during the analysis process, providing at least three opportunities to contaminate each probe: once to transfer the probe from a shipping container to a sample preparation platform, once to transfer the probe from the sample preparation platform to a mass spectrometer, and once to transfer the probe to storage. Each successive contact with the probe increases the likelihood of accidental contamination of the active surfaces, and consequent interference with analysis. Since many experimental procedures use numerous probes to obtain statistically relevant data and/or to analyze multiple analytes for comparison, contamination opportunities increase accordingly.

Furthermore, manual handling of individual probes substantially reduces throughput when multiple individual probes are desired to be analyzed.

In addition, because some mass spectrometers accept only one probe at a time, the operator must be present to exchange individual probes if the operator desires to analyze a plurality of probes.

Some known MS systems have attempted to increase throughput and reduce the need for operator presence during MS analysis by automating insertion and removal of sample carriers into and out of mass spectrometers. One example system is described in U.S. Reissue Pat. No. RE37,485, which shows a single sample cassette or magazine within which a plurality of sample carriers may be removably carried to await analysis.

Additional examples of MS systems that comprise only a single sample cassette or magazine are described in U.S. Pat. Nos. 4,405,860; 4,879,458 and 4,076,982. Those systems appear to require the operator to manually load the sample carriers into their respective sample magazine or cassette. While the semi-automation reduces the need for constant operator presence during actual analysis, there still remains the need for the operator to manually load the sample carriers into the sample cassette prior to analysis. Thus, the number of manual operations and contamination opportunities remain high.

These problems discussed above are characteristic not only of MS systems, but of many applications that require an operator to load sample probes into an analytical instrument.

Thus, it would be desirable to provide a device for automating transfer of multiple sample probes between a cassette within which the plurality of probes are initially constrained and an analytical instrument that would reduce the opportunities for accidental operator contamination of the samples.

It would also be desirable to provide a device for automating transfer of multiple sample probes between a cassette within which the plurality of probes are initially constrained and an analytical instrument that would reduce the number of manual operations performed by an operator.

It further would be desirable to provide a device for automating transfer of multiple sample probes between a cassette within which the plurality of probes are initially constrained and an analytical instrument that would permit continuous analysis of a plurality of sample probes.

It still further would be desirable to provide a device for automating transfer of multiple sample probes between a cassette within which the plurality of probes are initially constrained and an analytical instrument that would reduce, if not eliminate, the necessity for constant operator surveillance during analysis of the plurality of sample probes.

SUMMARY OF THE INVENTION

In view of the foregoing, it is an object of the present invention to provide a device for automating transfer of multiple sample probes between a cassette within which the plurality of probes are initially constrained and an analytical instrument that would reduce the opportunities for accidental operator contamination of the samples.

It is also an object of the present invention to provide a device for automating transfer of multiple sample probes between a cassette within which the plurality of probes are initially constrained and an analytical instrument that would reduce the number of manual operations performed by an operator.

It is a further object of the present invention to provide a device for automating transfer of multiple sample probes between a cassette within which the plurality of probes are initially constrained and an analytical instrument that would permit continuous analysis of a plurality of sample probes.

It is still a further object of the present invention to provide a device for automating transfer of multiple sample probes between a cassette within which the plurality of probes are initially constrained and an analytical instrument that would reduce, if not eliminate, the necessity for constant operator surveillance during analysis of the plurality of sample probes.

These and other objects of the present invention are accomplished by providing a loading device that may automatically transfer a plurality of probes, such as laser desorption/ionization probes, between a cassette within which the plurality of probes are initially constrained and an analytical instrument, such as a mass spectrometer. The loading device of the present invention may be configured to accept a plurality of cassettes each removably constraining a plurality of probes, or a single cassette removably constraining a plurality of probes. The loading device also may be configured to permit the plurality of cassettes to be independently interchanged with a separate cassette removably constraining a separate plurality of probes during analysis, or additional cassettes removably constraining a plurality of additional probes to be loaded into the device during analysis. Consequently, opportunities for contamination and the number of manual operations are decreased since the operator may now transfer multiple probes in one step without having to directly contact the probes, rather than having to directly handle each individual probe for manual transfer to and from the analytical instrument. Furthermore, because a cassette may be interchanged with a separate cassette or additional cassettes may be loaded during analysis, the analytical instrument may continuously analyze probes without interruption.

The loading device of the present invention comprises a frame disposed external to a probe receiving chamber integral to the analytical instrument, and a cassette transport assembly and a probe insertion assembly attached to said frame. In a useful embodiment, the cassette transport assembly may comprise cassette retention means to receive the cassette, and cassette translation means to linearly translate the cassette in a first axis to a defined insertion/removal position that aligns the cassette with respect to the chamber so that a select probe from the plurality of probes may be translated therebetween. In a useful embodiment, the probe insertion assembly may comprise engagement means to rotatably engage one of the plurality of probes, rotation means to rotate the engagement means, and probe translation means to translate the engagement means in a second axis orthogonal to said first axis, wherein translation of one of the plurality of probes along said second axis translates that probe between the cassette and the chamber. In certain embodiments, the cassette retention means may comprise a cassette support frame, the cassette translation means may comprise a linear actuator subassembly, the engagement means may comprise an engagement piece, the rotation means may comprise a rotary actuator subassembly, and the probe translation means may comprise a linear actuator subassembly.

The loading device of the present invention also may comprise a controller that accepts digital information, comprising a protocol that specifies the order in which each probe of the plurality of probes should be transferred into the analytical instrument for analysis, the controller configured to control said cassette transport assembly and said probe insertion assembly responsive to the digital information.

In another aspect of the present invention, the loading device also may comprise a spare probe slot integral with said cassette transport assembly, wherein said spare probe slot may accept a single spare probe. The controller may direct said cassette transport assembly to position said spare probe slot with respect to the chamber, the position permitting the spare probe to be inserted into or removed from said spare probe slot. This is particularly beneficial when the loading device unsuccessfully attempts to load said probe into the analytical instrument or when the operator removes the cassette from which the probe was originally extracted prior to analysis completion of said displaced probe. This permits the device to continue with analysis of the remaining probes, rather than ceasing analysis upon generation of an error condition when the displaced probe is unable to be reinserted. Alternatively, the spare probe slot may be used to actuate immediate analysis of a "high priority" probe that is not constrained within a cassette by placement of the "high priority" probe within the spare probe slot and interruption of the established protocol.

In a useful embodiment, the loading device further may comprise a housing having a plurality of doors that permit the operator to access the cassette transport assembly to deposit or remove one or more cassettes and/or a spare probe. The housing further comprises a plurality of sensors that may detect whether the housing is properly placed and the plurality of doors are closed. If the sensors detect improper placement or open doors, the controller inhibits actuation of the loading device to protect the operator from moving parts. In certain embodiments, the loading device also may have additional safety features, such as a flexible belt that partially blocks access to the loading device when a cassette is in transit therein, or a gate that prevents a cassette from being loaded into the device and protects the operator from moving parts when the cassette retention means is not positioned to accept the cassette.

In a useful embodiment, the probe insertion subassembly further may comprise a cover plate that concurrently may be rotated with the engagement means and/or configured to sealingly cover the analytical instrument to sustain a vacuum therein.

Methods of operating the loading device of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, in which wires and cables from electrical components may have been disengaged for illustrative purposes, and in which:

FIG. 5A is a front, top perspective view of the probe insertion assembly of a first embodiment of the loading device of the present invention;

FIG. 5B is an enlarged view of a select area of FIG. 5A, denoted by the dotted lines;

FIGS. 8A–B are perspective views of a second embodiment of the probe insertion assembly of the present invention;

FIGS. 10A–B respectively are assembled and exploded perspective views of a cassette retention subassembly of the cassette transport assembly of a second embodiment of the loading device of the present invention;

FIG. 10C is a perspective view of a cam follower of a cassette retention subassembly of a second embodiment of the loading device of the present invention;

FIGS. 11A–B respectively are assembled and exploded perspective views of a shuttle of a cassette transport assembly of a second embodiment of the loading device of the present invention;

FIGS. 12C–D respectively are assembled and exploded perspective views of elements of the probe insertion assembly of FIG. 12A;

DETAILED DESCRIPTION OF THE INVENTION

The following description uses MS as an illustrative application, describing transfer of a plurality of probes between a cassette within which the plurality of probes are initially constrained and a mass spectrometer. Of course, one of ordinary skill in the art will recognize that the automatic loading device and methods of the present invention may be used with any analytical instrument that requires transfer of multiple sample probes thereto, particularly when an increase in throughput and reductions in sample contamination opportunities and operator presence are desired.

Figure 1A:
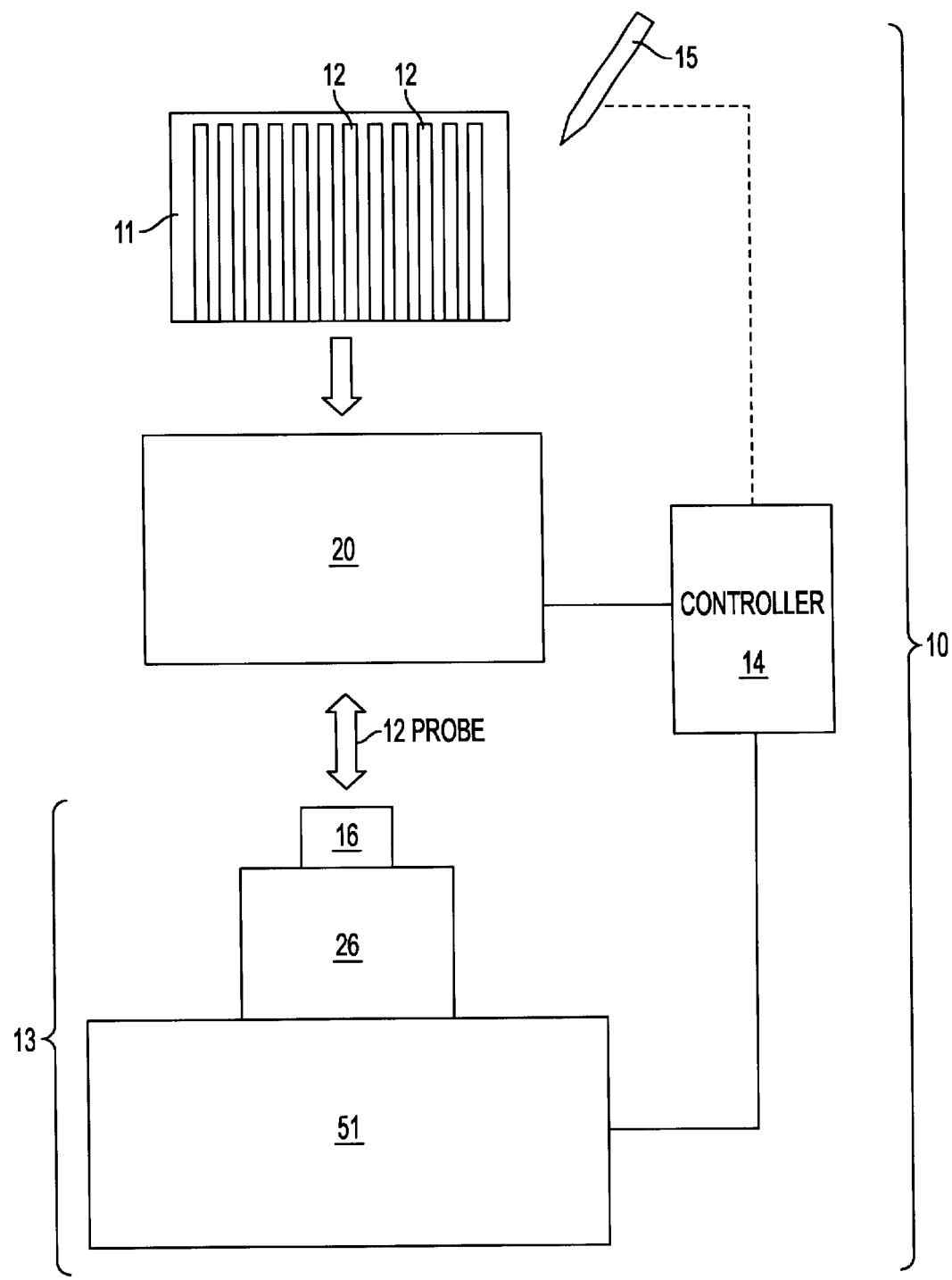
FIG. 1A is a schematic illustration of a mass spectrometric system, including the loading device of the present invention.

Referring to FIG. 1A, mass spectrometric system 10, including loading device 20 of the present invention, is schematically depicted. Mass spectrometric system 10 includes at least one cassette 11 within which a plurality of sample probes 12 are constrained. Each probe 12 typically comprises a plurality of active (e.g. affinity capture) surfaces to which analytes may be adsorbed. Samples may be deposited onto the active surfaces either by an operator or by sample preparation robotics 15 known in the industry that are designed to automatically deliver fluid samples, e.g. to microtiter plates. Once the samples are deposited on probe 12 and optionally further processed for analysis, cassette 11 may be inserted into loading device 20 of the present invention, which then automatically loads each probe 12 into mass spectrometer 13 for analysis. In certain embodiments, mass spectrometer 13 may comprise a probe receiving chamber 26 that may sustain a vacuum independently of an ion source chamber 51, and a receiving post 16 that accepts probe 12 for transfer between probe receiving chamber 26 and ion source chamber 51. As would be apparent to one of ordinary skill in the art, analytical instrument 13 may be provided without chamber 26, and probe 12 may be received directly within ion source chamber 51.

Loading device 20 of the present invention may accept a plurality of cassettes 11 each constraining a plurality of probes 12, and may permit each cassette 11 to be independently interchanged with a separate cassette 11 that removably constrains a separate plurality of probes 12 during mass spectrometric analysis or permit additional cassettes 11 to be loaded into device 20 during mass spectrometric analysis. Advantageously, opportunities for contamination and the number of manual operations are decreased since the operator may now transfer multiple probes in one step without having to handle each individual probe 12 for manual transfer to and from the mass spectrometer, and indeed without having directly to contact any of the probes. Furthermore, because a cassette may be interchanged with a separate cassette or additional cassettes may be loaded during MS analysis, mass spectrometer 13 may continuously analyze probes without interruption. Furthermore, because probes 12 are carried within cassette 11 and device 20 may be configured to accept a plurality of cassettes 11, the operator can avoid contamination of the samples deposited on probes 12 by handling the cassettes, and not the probes.

Mounted on mass spectrometer 13, device 20 automates the individual transfer of each probe 12 between a cassette 11 and mass spectrometer 13 without necessitating operator surveillance. Controller 14, which may comprise a microprocessor or an ASIC, or which may be controlled by non-integral computing means, may control both device 20 and mass spectrometer 13 to, inter alia, facilitate transfer therebetween. If system 10 utilizes a sample preparation robot 15, controller 11 also may control robot 15 to centralize command.

Figure 1B:
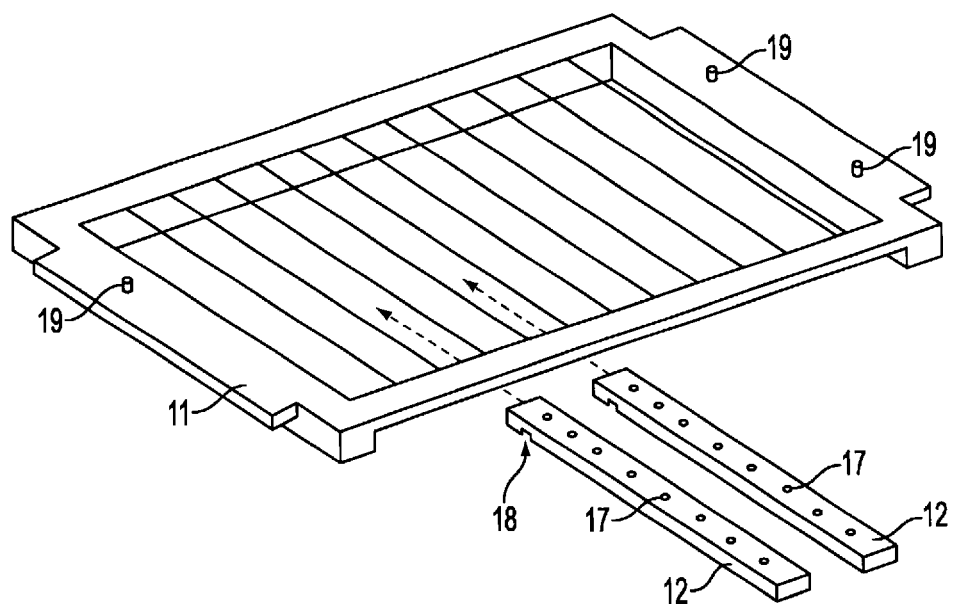
FIG. 1B is a representative depiction of a cassette and probes of the mass spectrometric system that is compatible with the loading device of the present invention.

Representative depictions of cassette 11 and probes 12 that are compatible with loading device 20 of the present invention are shown in FIG. 1B. Cassette 11 constrains a plurality of probes 12 such that the longitudinal centerlines of probes 12 are parallel. Each probe 12 comprises a plurality of active surfaces 17 and at least one groove 18 that may be mechanically engaged with an engagement mechanism of loading device 20 to be described hereinbelow. Each cassette 11 may have one or more alignment pins 19 that are disposed on an upper surface of the cassette. When a plurality of cassettes are stacked together, the alignment pins are configured to mate with alignment holes (not shown) disposed on one or more lower surfaces of adjacent cassettes. The alignment holes also may be employed to align the cassettes with loading device 20 in a manner to be described in greater detail hereinbelow. Advantageously, cassette 11 may be used to carry plurality of probes 12 throughout sample preparation, MS analysis, and sample storage without the need to remove the probes from the cassette, again dramatically reducing the number of manual operations required, consequently reducing contamination opportunities. Exemplary cassettes and probes suitable for use with the apparatus of the present invention are described in greater detail in co-pending, to be commonly-assigned U.S. patent application Ser. No. 10/375,213, filed Feb. 25, 2003, and U.S. provisional patent application Ser. No. 60/359,940, filed Feb. 26, 2002, the entireties of which are incorporated by reference herein.

Figure 1C:
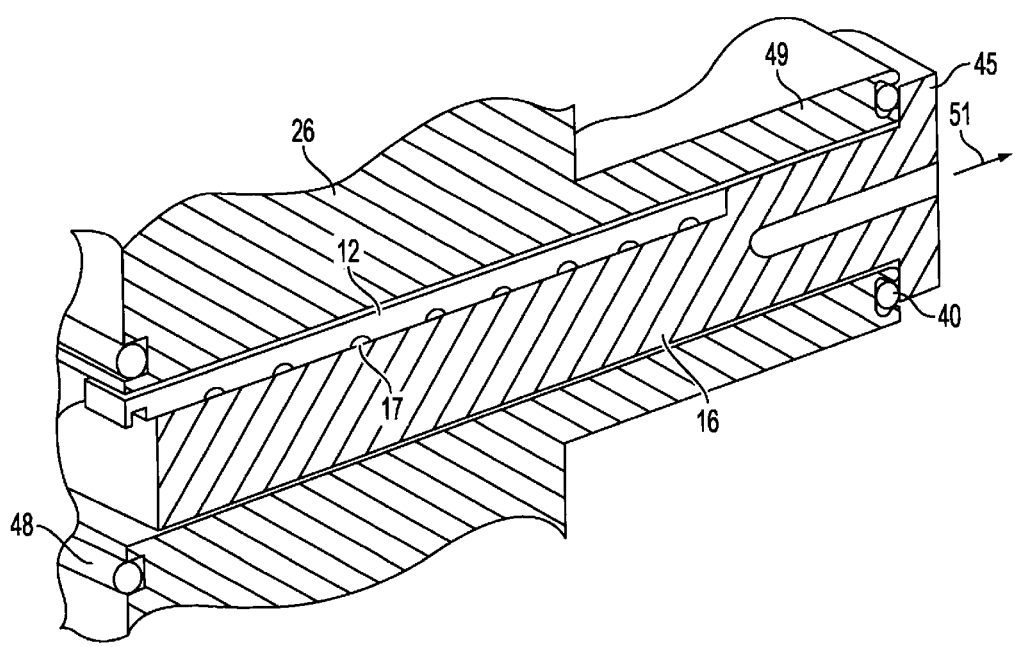
FIG. 1C is a representative sectional view of a receiving post that is compatible with the loading device of the present invention.

FIG. 1C illustrates a representative sectional view of receiving post 16 that may be suitable for use in certain embodiments. For illustrative purposes, FIG. 1C may omit some details. Receiving post 16 may comprise, inter alia, a receptacle for receiving and constraining one or more probes 12, and a seal 40, e.g., an o-ring or other elastomeric seal known in the art, disposed within a stationary structure 49. Seal 40 actively may be engaged by receiving post 16 to permit probe receiving chamber 26 to be vented to atmospheric pressure while a vacuum is sustained in ion source chamber 51. In a useful embodiment, receiving post 16 may incorporate a flange 45 that is configured to press against seal 40 when chamber 26 is ready to vent to atmospheric pressure and the receiving post is disposed to permit loading device 20 to engage probe 12 for transfer between receiving post 16 and a cassette 11. When flange 45 of post 16 is pressed against seal 40, probe receiving chamber 26 is sealed off from ion source chamber 51. Sealing engagement between flange 45 and seal 40 may be released when receiving post 16 translates probe 12 away from stationary structure 49 and probe receiving chamber 26 to ion source chamber 51, after probe receiving chamber 26 pumps down to a predetermined pressure. Probe receiving chamber 26 also may include additional seals 48, e.g., o-rings or other elastomeric seals known in the art, to maintain a vacuum in probe receiving chamber 26 when desired. Advantageously, this permits probe receiving chamber 26 to vent to atmospheric pressure with each load cycle, while obviating the need to vent ion source chamber 51 for each load cycle. As would be apparent to one of ordinary skill in the art, while receiving post 16 is shown as an elliptical cylinder in the embodiment of FIG. 1C, the receiving post may be configured in any shape suitable for accepting and translating a probe 12 therein.

Figure 2:
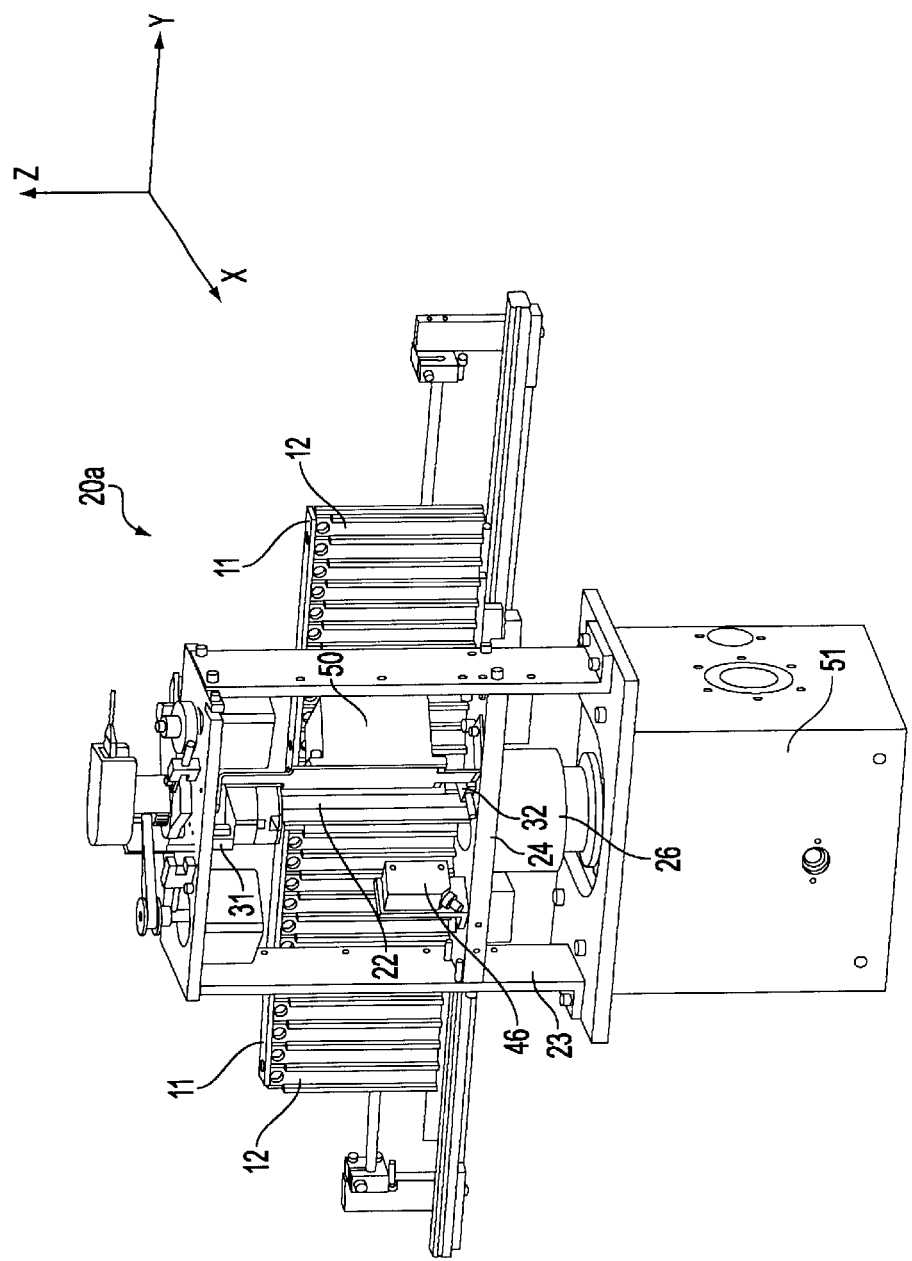
FIG. 2 is a front perspective view of a first embodiment of the loading device of the present invention.

Referring to FIG. 2, a first embodiment of the loading device of the present invention is described. Loading device 20a comprises frame 23, having lower support plate 24, upon which components of a cassette transport assembly and a probe insertion assembly may be mounted. The cassette transport assembly linearly translates one or more cassettes 11 in the Y axis so that one of probes 12 constrained therein may be positioned for engagement with the probe insertion assembly, or, alternatively, so that one of probes 12 may be reinserted into cassette 11 after analysis completion. The probe insertion assembly rotatably engages said probe 12 for transfer thereof in the Z axis between cassette 11 and probe receiving chamber 26 of mass spectrometer 13 (see FIG. 1). These assemblies are described in greater detail hereinafter. It will be apparent to one of ordinary skill in the art that, while FIG. 2 shows that frame 23 comprises a single structure upon which both cassette and probe insertion assemblies are mounted, frame 23 may comprise multiple structures, perhaps a separate structure for each assembly.

Figure 3:
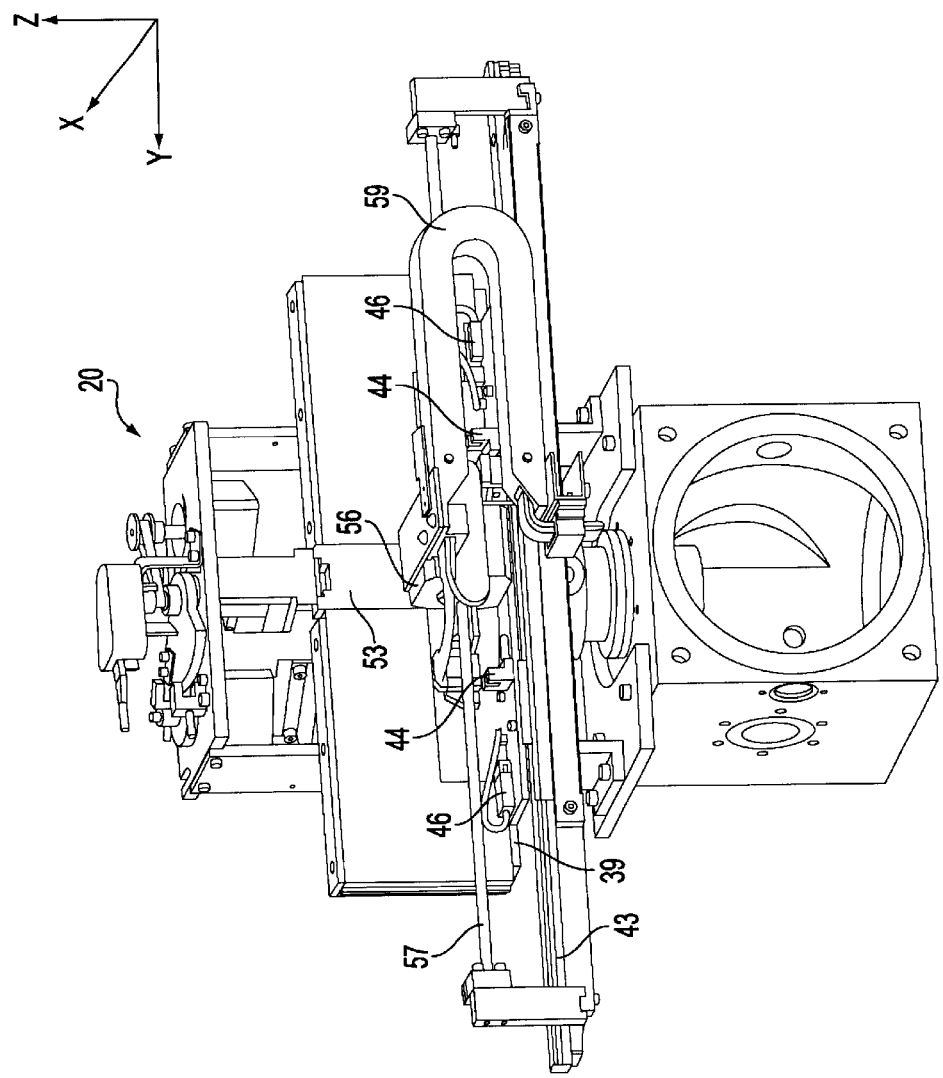
FIG. 3 is a rear perspective view of a first embodiment of the loading device of the present invention.
Figure 4A:
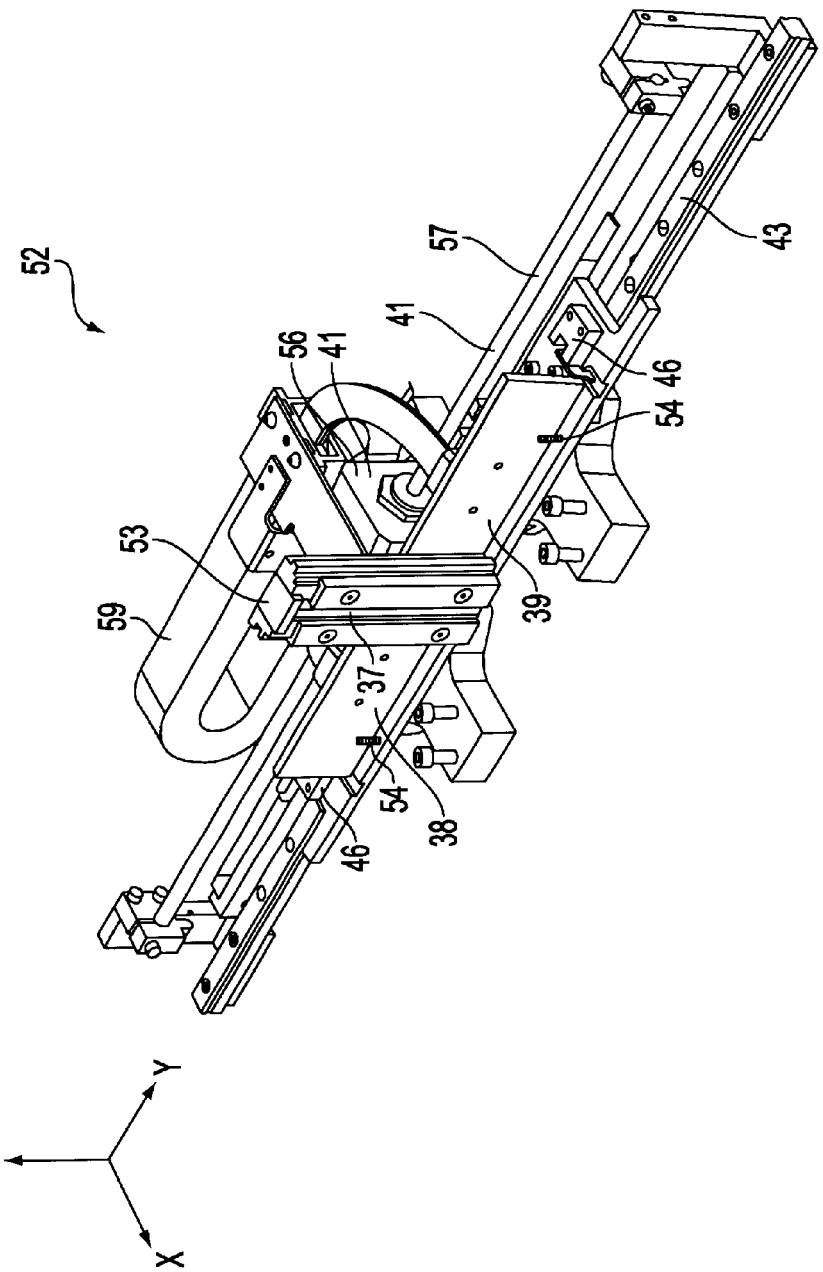
FIGS. 4A–B are, respectively, front and rear perspective views of the cassette transport assembly of a first embodiment of the loading device of the present invention.
Figure 4B:
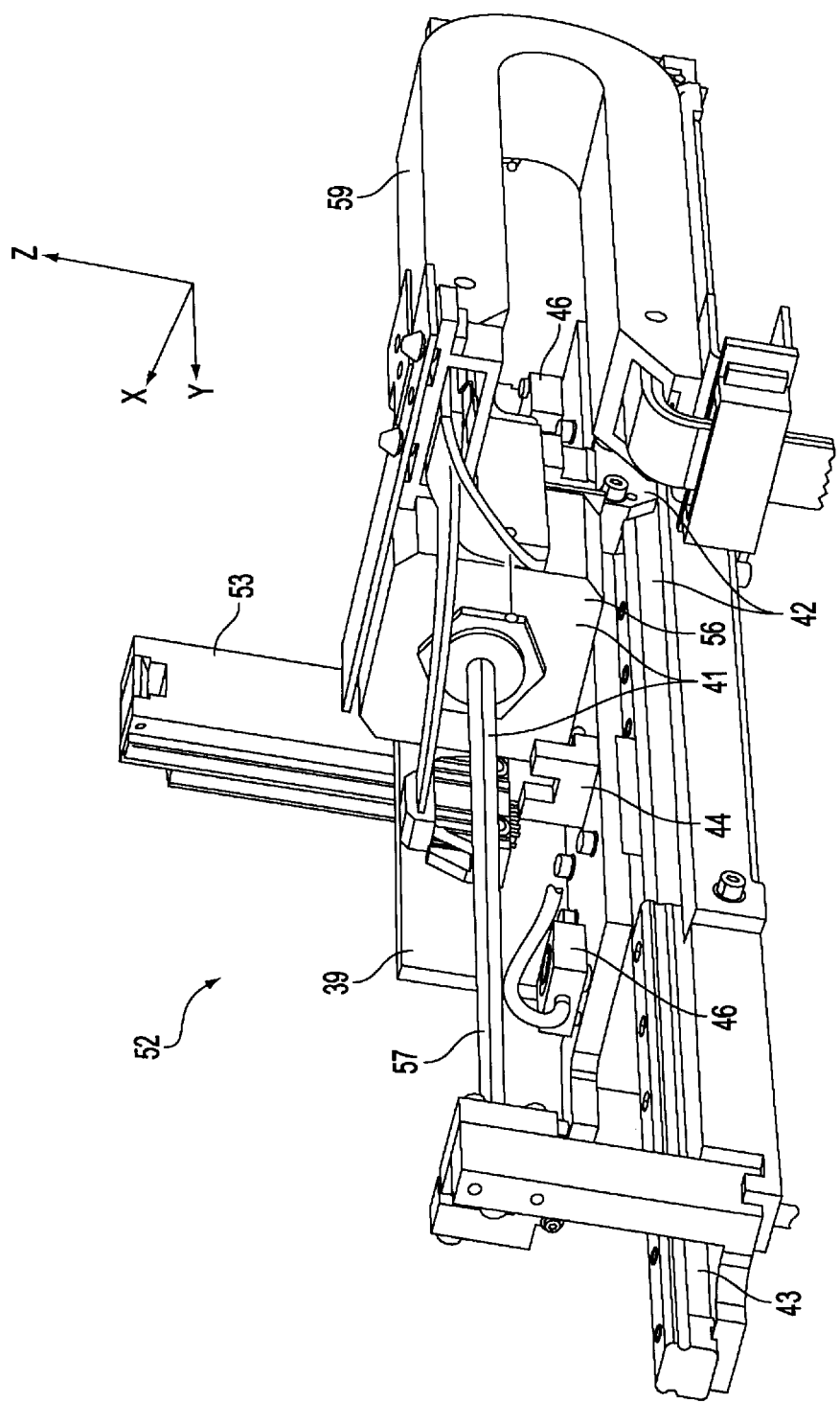

In FIGS. 3 and 4A–B, cassette transport assembly 52 is illustrated. In a useful embodiment, cassette transport assembly 52 comprises, inter alia, carrier components that include a spare probe holder 53 having a spare probe slot 37 that accepts a single probe 12, a left cassette support plate 38 that accepts a cassette 11 in a left cassette position, and a right cassette support plate 39 that accepts a cassette 11 in a right cassette position. Each support plate 38 and 39 may comprise at least one pin 54 to engage a cassette 11 to each support plate. Spare probe slot 37 may be used to receive a probe 12 that device 20a had extracted from cassette 11 but is unable to reinsert therein. This may occur when device 20a unsuccessfully attempts to load probe 12 into mass spectrometer 13 after the probe had been extracted from cassette 11, or when cassette 11, from which probe 12 had been extracted, is removed from device 20a prior to completion of analysis. Upon occurrence of such conditions, controller 14 signals device 20a to deposit said probe 12 into spare probe slot 37 and then alerts the operator to remove the displaced probe. Advantageously, this permits mass spectrometric system 10 to automatically operate without constant operator surveillance and/or a cessation in analysis upon occurrence of a displaced probe.

Spare probe slot 37 also may be used to accept a "high priority" probe 12 for immediate analysis. To actuate this function, the operator instructs controller 14 via a user interface (not shown) to actuate cassette transport assembly 52 to position spare probe slot 37 for receipt of "high priority" probe 12 from the operator. Once analysis of a probe 12 currently in mass spectrometer 13 is completed and reinserted into its corresponding cassette 11, "high priority" probe 12 may then be transferred to mass spectrometer 13 for analysis, and, upon completion, returned to spare probe slot 37 for removal by the operator.

Note that while FIGS. 2–4B may depict one configuration of spare probe slot 37 and support plates 38 and 39, different permutations and numbers of carrier components may be embodied without departing from the invention. For example, device 20a of the present invention may accept more than two cassettes 11 and one spare probe 12.

In addition to carrier components, cassette transport assembly 52 also comprises translational components that actuate and facilitate translation. In a typical embodiment, the translational components comprise a linear actuator 41 to translate the carrier components in the Y axis, a linear encoder 42 to track the position of linear actuator 41, a track 43 that guides the linear translation, and position sensors 44 to signal the ends of actuator travel to controller 14. Linear actuator 41 comprises a lead screw assembly having a motor-driven lead nut 56 and a screw 57 upon which lead nut 56 travels. In operation, screw 57 remains stationary while a motor integral to lead nut 56 rotates about screw 57. Lead nut 56 is rotationally constrained by being mounted to cassette support plates 38 and/or 39 so that movement thereof is limited to the Y axis. One of ordinary skill in the art will recognize that, not only may other constraining means be used, other linear actuators 41 may be used in place of the lead screw assembly shown here without departing from the present invention. For example, a motor-driven pulley assembly or a telescoping arm assembly also may serve to linearly actuate cassette transport assembly 52.

Linear encoder 42 may comprise a fixed ruler upon which graduations are disposed, and an optical sensor mounted approximately underneath lead nut 56 and that travels therewith, counting the graduations on the ruler as linear actuator 41 translates the carrier components. In a useful embodiment, the graduations may have a resolution of 360 lines per inch. Alternatively, cassette transport assembly 52 may use other means to track the position of lead nut 56. One useful embodiment may utilize open loop machine control in which controller 14 counts the number of steps or intervals lead nut 56 travels from a defined home position. The steps or intervals correspond to the linear displacement of lead nut 56 from the home position. For example, if a stepper motor is used, the steps of the stepper motor may be correlated to linear displacement of lead nut 56 from the home position. Other tracking means include position sensors, such as resistive potentiometers, capacitive displacement sensors, or a rotary encoder.

Cassette transport assembly 52 additionally comprises a cassette detection sensor 46 for each cassette 11 that device 20a is configured to accept. Each cassette detection sensor 46 may be used to indicate to controller 14 that cassette 11 is present for analysis or that cassette 111 has been removed. The latter function facilitates controller 14 in directing device 20a to actuate insertion of any probe 12 currently being analyzed by mass spectrometer 13 into spare probe slot 37 if its corresponding cassette 11 is removed prior to analysis completion. In a useful embodiment, cassette detection sensors 46 may comprise photoelectric switches, or also may comprise other contact and non-contact sensors such as force/strain, pressure, or piezoelectric sensors.

Figure 5C:
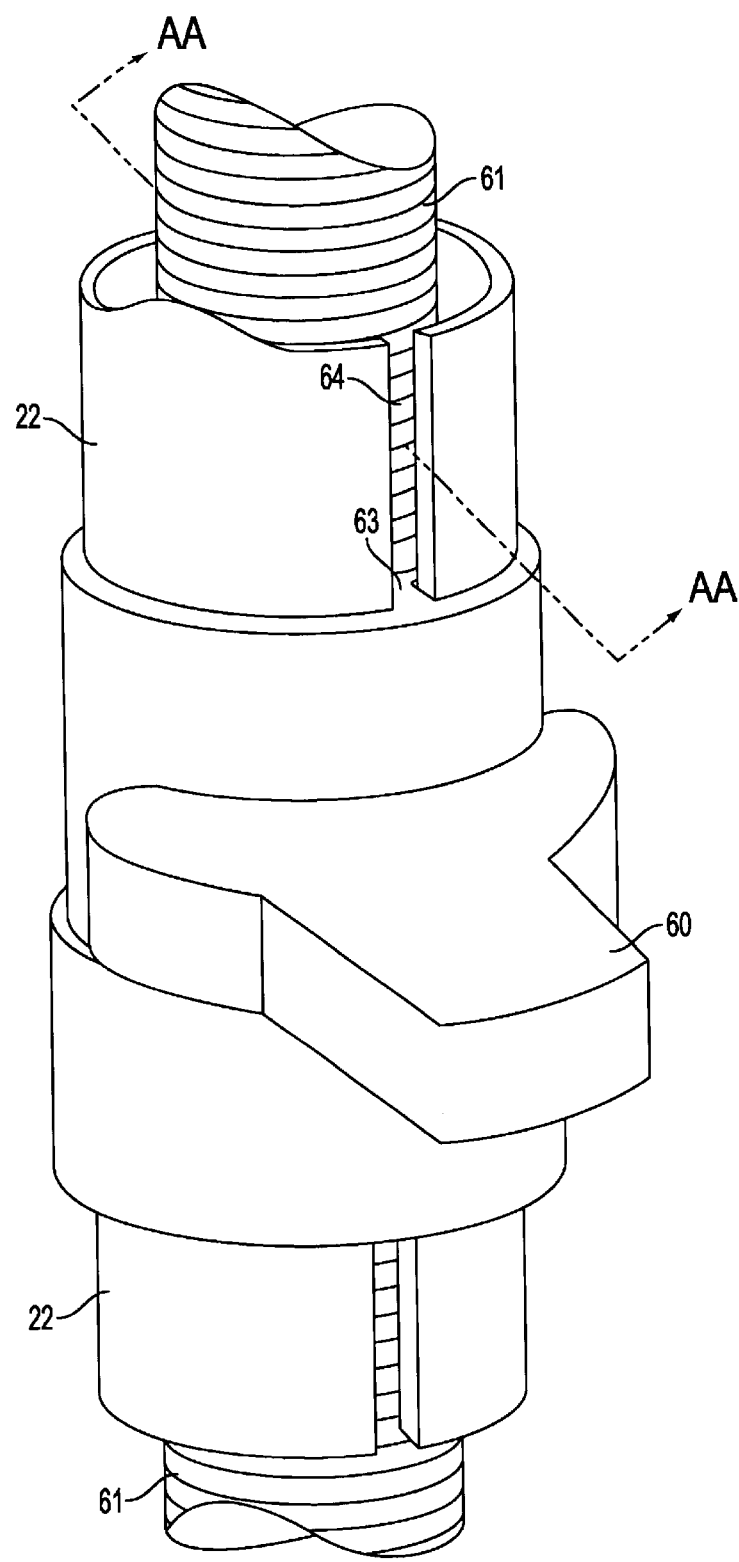
FIGS. 5C–D are perspective, close-up views of select components of the probe insertion assembly of a first embodiment of the loading device of the present invention.
Figure 5D:
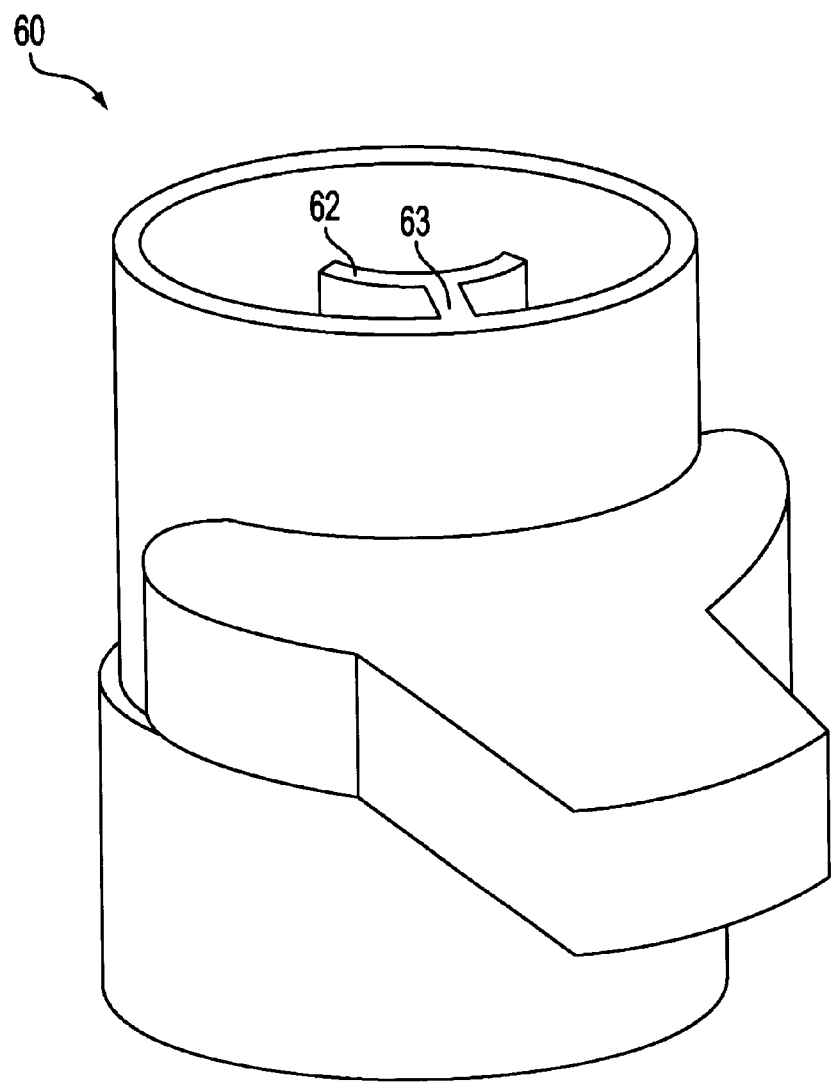
Figure 5E:
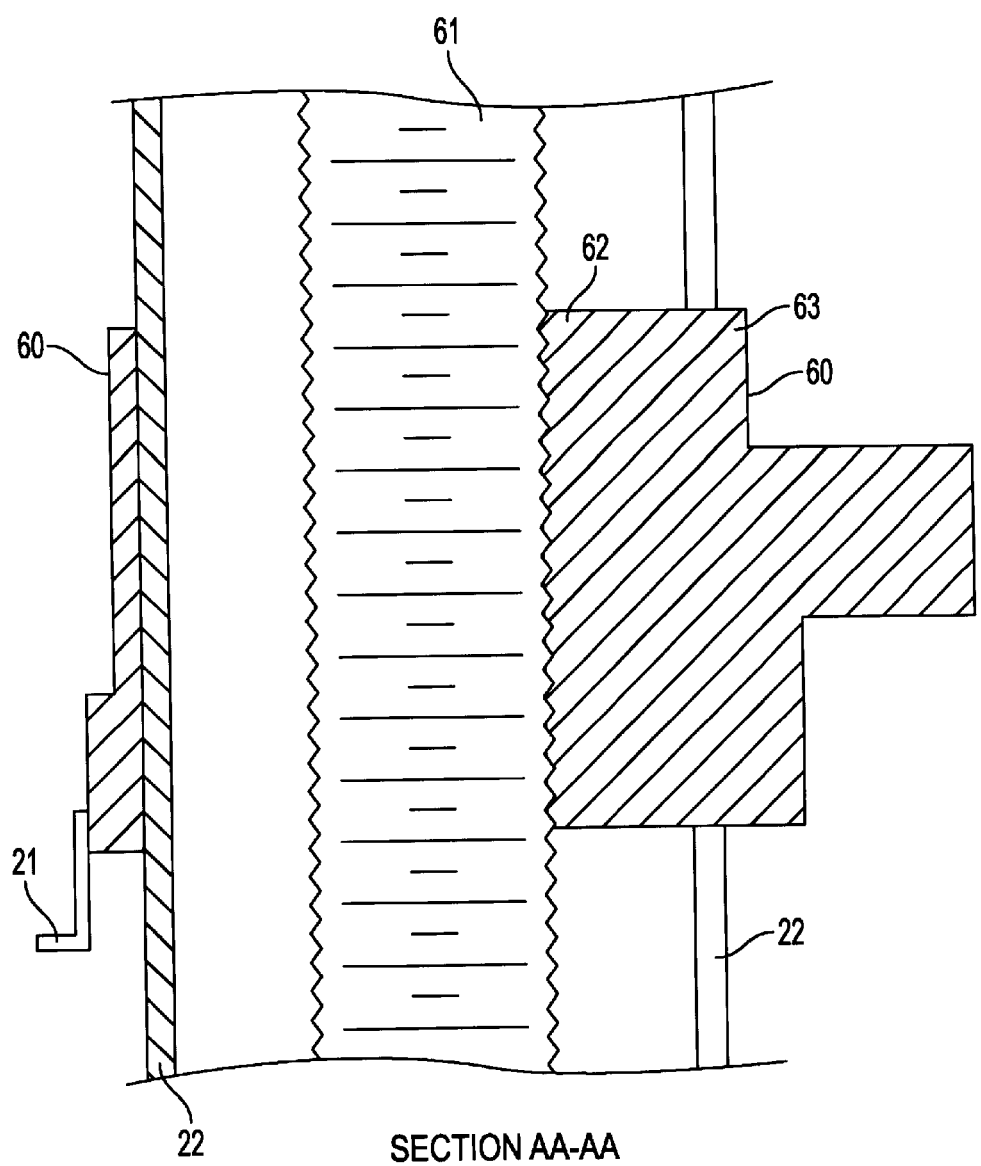
FIG. 5E is a section view of FIG. 5C and denoted as section AA—AA therein.

In FIGS. 5A–H, probe insertion assembly 55 is illustrated, the assembly comprising a probe hook 21 to rotatably engage groove 18 of a probe 12, a probe translation subassembly to linearly translate a probe 12 in the Z axis between chamber 26 and cassette 11, and a probe rotation subassembly to rotate probe hook 21 in a plane orthogonal to the Z axis for engagement with probe 12. The probe translation and rotation subassemblies, while serving different functions of probe insertion assembly 55, share common elements—a rail 22 comprising a hollow shaft and a lead nut 60 slidably engaged thereto and upon which probe hook 21 is fixedly attached. Shown in FIGS. 5C–E, the probe translation subassembly further comprises a screw 61 having a centerline disposed parallel to rail 22, wherein the screw, along with rail 22 and lead nut 60, comprise a screwrail that functions as the linear actuator of the probe translation subassembly. Lead nut 60 comprises an engagement portion 62 having threads thereon that engage the threads disposed on screw 61. It will be apparent to one of ordinary skill in the art that, while FIGS. 5D–E illustrate an engagement portion 62 that engages only a portion of the circumference and length of screw 61, an engagement portion 62 that fully circumscribes or engages more or fewer threads of screw 61 would not deviate from the present invention. Furthermore, it also should be apparent that, while the present figures depict a hollow shaft, rail 22 may comprise numerous different configurations without departing from the present invention.

Screw 61 is rotated by concerted action of a timing belt 27, a motor 28, a first timing belt gear or pulley 29 fixedly coupled to motor 28, and a second timing belt gear or pulley 30 fixedly coupled to screw 61. Shown in FIGS. 5F–G, timing belt 27 connects first gear 29 to second gear 30. When motor 28 rotates first gear 29, timing belt 27 forces rotation of second gear 30, which in turn rotates screw 61. To rotationally constrain lead nut 60 from rotating with screw 61, and thereby limit movement of lead nut 60 to the Z axis when linear translation is desired, a slot 64 (see FIG. 5C), disposed along the longitudinal length of rail 22, engages a flange 63 integral to lead nut 60. The width of slot 64 is dimensioned to permit flange 63 to translate therealong but to restrict flange 63 from any rotational movement with respect thereto. Thus, when screw 61 is rotated, the walls of slot 64 serve as a track that establishes movement of lead nut 60 in the Z axis.

To determine and alert controller 14 to the upper and lower limits of probe hook 12 travel, two additional sensors—upper limit sensor 31 and lower limit sensor 32 (see FIGS. 2 and 5H)—are disposed at longitudinally opposing ends of rail 22. Detection by upper limit sensor 31 demarcates proper positioning of probe hook 21 for engagement with or disengagement from probe 12 when probe 12 is fully constrained within cassette 11. Detection by lower limit sensor 32 demarcates proper positioning of probe hook 21 for engagement with or disengagement from probe 12 when probe 12 is fully constrained within receiving post 16. Upon receipt of a signal from one of two sensors 31 or 32, controller 14 may terminate continued linear actuation of probe hook 21 immediately or after actuation of an additional predetermined distance. In a useful embodiment, sensors 31 and 32 may be photoelectric sensors, but may also comprise other contact and non-contact sensors known in the art. A rotary encoder 58 also may be used in conjunction with sensors 31 and 32 to track the linear position of lead nut 60.

Figure 5F:
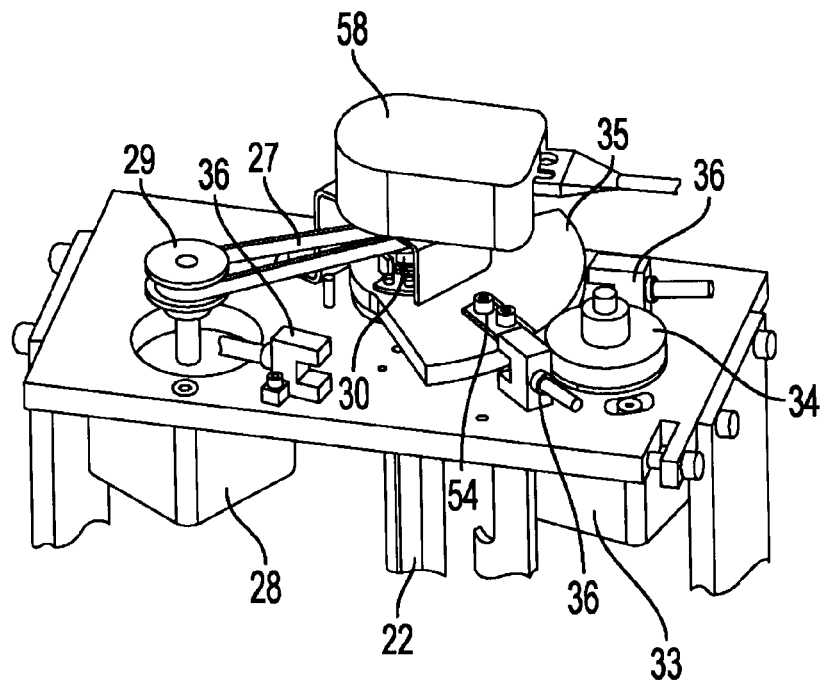
FIGS. 5F–G are, respectively, rear and front, partial perspective views of elements of the probe insertion assembly of a first embodiment of the loading device of the present invention.
Figure 5G:
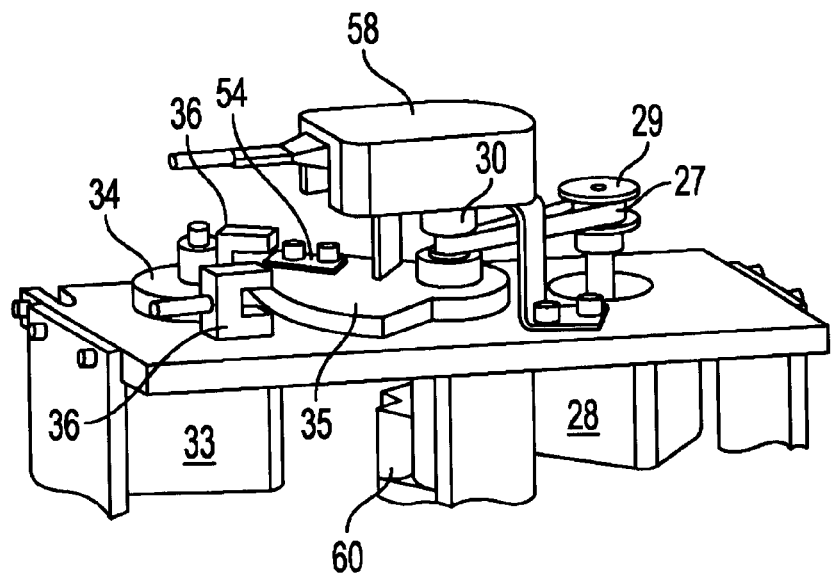
Figure 5H:
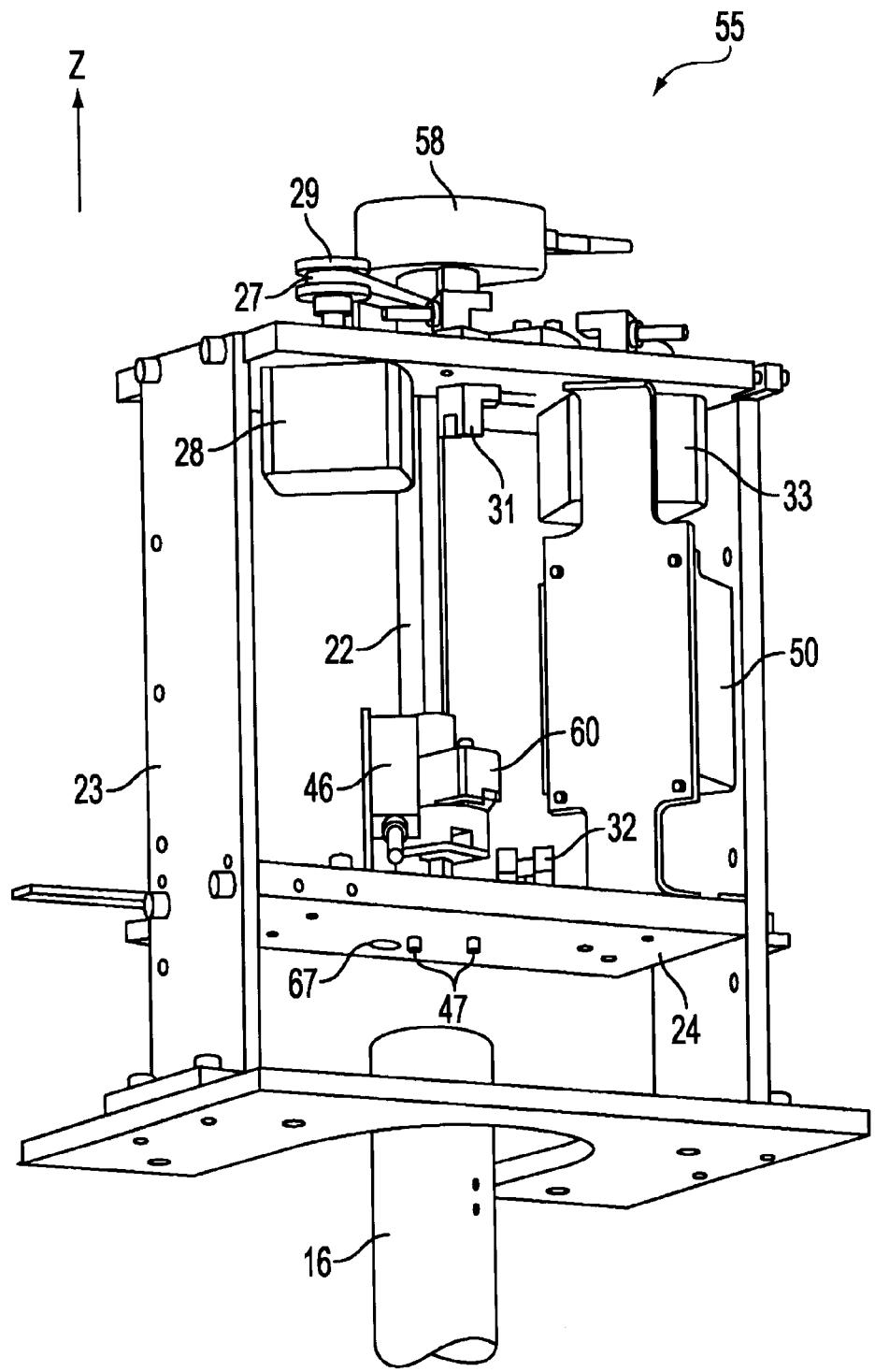
FIG. 5H is a rear, bottom perspective view of the probe insertion assembly of a first embodiment of the loading device of the present invention.

In addition to rail 22 and lead nut 60, the probe rotation subassembly further comprises a motor 33, a gear 34 fixedly coupled to motor 33, and a sector gear 35 rotatably engaged to gear 34 and fixedly coupled to rail 22 (see FIGS. 5F–G). When motor 33 rotates gear 34, sector gear 35 is consequently rotated in the opposite direction, thereby also rotating rail 22 attached thereto. When rail 22 is rotated about the centerline of screw 61, slot 64 disposed therealong provides a force against flange 63, which causes flange 63, and thereby lead nut 60, to rotate therewith. Since probe hook 21 is rigidly connected to lead nut 60, it too is concurrently rotated. A useful embodiment may utilize the travel of lead nut 60 in the Z direction during rotation of probe hook 21 to ensure successful engagement thereof with groove 18 of probe 12. This prevents probe hook 21 from "hanging up" on the edge of groove 18. Alternatively, when lead nut 60 is rotated along with rail 22, screw 61 may remain stationary. In that case, the pitch of screw 61 may be designed so that the travel of lead nut 60 in the Z axis is negligible. As would be apparent to one of ordinary skill in the art, however, other means may be used to ensure that probe hook 21 aligns with groove 18 upon rotatable engagement thereof. As further would be apparent, the probe hook also may be designed to engage the probe by means other than rotational means. For example, lead nut 60 may be coupled to a protuberance that is actuated to linearly advance into groove 18 to engage probe 12 and to linearly retreat from groove 18 to disengage probe 12.

To determine the angular position of probe hook 21, device 20a may comprise a plurality of position sensors 36, which are shown most clearly in FIG. 5F. A useful embodiment may comprise a plurality of photoelectric sensors, which may be actuated by a flag 54 disposed on sector gear 35. Sensors 36 also may comprise other contact or non-contact sensors known in the art. Signals from sensors 36 are relayed to controller 14, which in turn controls motor 33 responsive thereto. In a useful embodiment, three sensors may be disposed at intervals of 45 degrees to demarcate ends-of-travel and medial rotation positions. Alternatively, a resistance potentiometer, a capacitive displacement sensor, or a rotary encoder also may be used. A further alternative embodiment may use open loop control, in which motor 33 counts the number of steps or intervals from a home position. For example, if motor 33 comprises a stepper motor, the steps of the stepper motor may correlate to the angular displacement from the home position. A sensor 36 may be used with open loop control to alert controller 14 to an end-of-travel position or to a medial rotation position. One advantage of providing sensor 36 at the medial rotation position is that, when sensor 36 is triggered, controller 14 may recalibrate the intervals it has counted, thereby correcting any drift or error.

In addition to probe hook 21, rail 22 is also coupled to a cover plate 25 that is disposed to cover probe exchange port 67 (see FIGS. 5A–B). When the probe rotation subassembly is actuated, it concurrently rotates both cover plate 25 and probe hook 21 in their respective planes orthogonal to the Z axis. Probe exchange port 67 is disposed through lower support plate 24, provides a portal through which probe 12 may enter or exit probe-receiving chamber 26, and is aligned with a receiving post 16. Receiving post 16 aligns with probe exchange port 67 by interfacing with a plurality of pins 47 disposed on the underside of lower support plate 24 (see FIG. 5H). Alignment pins 47 may be cylindrically or frustoconically shaped with rounded or beveled ends. Note that, if the present loading device is used with an analytical instrument other than mass spectrometer 13 described herein, probe exchange port 67 may be disposed over a probe receiving entrance to that analytical instrument. In a useful embodiment, cover plate 25 serves as a valve to sustain a vacuum within chamber 26. Mechanical means, such as a spring or ramp, may facilitate sealing engagement by applying pressure to cover plate 25, thereby acting as a clamp. Cover plate 25 may comprise a viton gasket vulcanized onto a stainless steel plate, or other means to seal a vacuum system known to one of ordinary skill in the art.

In a useful embodiment, probe insertion assembly 55 also may comprise a probe detection sensor 46 (see FIGS. 2 and 5D) that may be used to detect the presence of probe 12 when constrained within cassette 11. Probe detection sensor 46 may comprise a photoelectric switch, or an indicia reader 50, as discussed in greater detail hereinbelow.

Figure 6A:
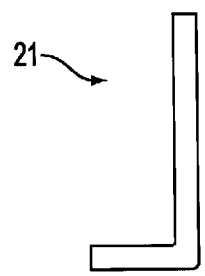
FIGS. 6A–B are profile views of different embodiments of a probe hook of the present invention.
Figure 6B:
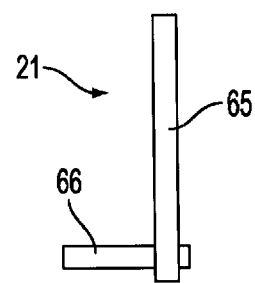

FIGS. 6A–B provide profile views of different embodiments of probe hook 21. FIG. 6A illustrates a unitary hook, while FIG. 6B depicts a hook made of two pieces. The latter embodiment comprises an extension piece 65 and an engagement piece 66. One of ordinary skill in the art will recognize that probe hook 21 may be any protuberance that is capable of engaging groove 18 of probe 12.

Figure 7:
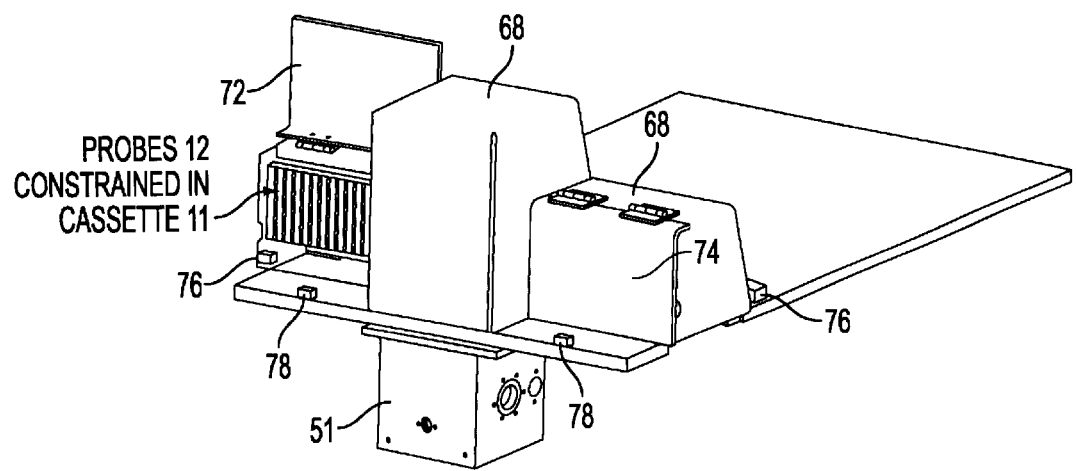
FIG. 7 is a perspective view of a housing suitable for the loading device of the present invention.

Referring to FIG. 7, housing 68 of the present invention is described, comprising a removable central unit 70, a left access door 72, and a right access door 74. Access doors 72 and 74 are coupled to central unit 70 and may be rotatably opened to access the left and right cassette positions, respectively. Should the operator want to exchange one or more cassettes 11 during mass spectrometric analysis of a probe 12 or when device 20a is otherwise idle, the operator may do so through doors 72 and 74. Device 20a also comprises a plurality of sensors 76, such as photoelectrical switches or other contact/non-contact sensors, that communicate with controller 14 to detect that central unit 70 is in place and access doors 72 and 74 are closed prior to actuation of all or part of device 20a. If controller 14 determines that housing 68 is not properly located or that access doors 72 and 74 are not closed, controller 14 may inhibit actuation of linear actuator 41 of cassette transport assembly 52 and motors 28 and 33 of probe insertion assembly 55 until housing 68 is properly positioned and/or access doors 72 and 74 are closed. Advantageously, this protects the operator from moving parts.

In addition to receiving signals from sensors and in order to direct actuation of the cassette transport assembly 52 and probe insertion assembly 55, controller 14 may accept additional information that facilitates the transfer process, including a protocol that defines, inter alia, a queue that specifies the number and positions of probes 12 constrained within each of cassettes 11 and the order in which each probe 12 should be transferred into mass spectrometer 13 for analysis. Protocol information may be obtained from identifying indicia disposed on each cassette 11. Identifying indicia may include but are not limited to bar codes, magnetically-coded indicia, radiofrequency indicia (RFID tags) or other indicia known in the art that are capable of storing information. Accordingly, a useful embodiment of the present invention may comprise one or more indicia readers 50 (see FIG. 2). Alternatively, protocol information may be obtained from operator input via a user interface (not shown). The operator may either manually input appropriate information directly into controller 14 or download the information via a diskette or an intra- or inter-net. The operator also may choose to queue probes 12 in a random order. If a queue is not specified, device 20a may sequentially transfer each probe 12 from one or more cassettes 11 into mass spectrometer 13 for analysis, beginning with the probe constrained in the leftmost or rightmost position.

In addition to indicia disposed on cassette 11, indicia reader 50 may also obtain information from identifying indicia disposed on probes 12. As discussed above, indicia reader 50 may function in this capacity to identify the presence of a select probe 12 to be translated. Information encoded within the identifying indicia disposed on cassette (s) 11 and probes 12 may include means to identify the type of active surface on each probe 12, an analysis and/or data acquisition protocol associated with each probe, and tracking and sample information. Identifying indicia may further provide a unique identifier to associate results of analysis.

In a typical operation, the operator first indicates to controller 14 whether he or she wishes to insert one or two cassettes 11 into device 20a. If the operator chooses to insert only one cassette 11, linear actuator 41 may position either left cassette support plate 38 or right cassette support plate 39 for receipt of the one cassette 11 through either left access door 72 or right access door 74, respectively. Should the operator desire to insert two cassettes 11, linear actuator 41 first positions left cassette support plate 38 for receipt of first cassette 11 through left access door 72 and then positions right cassette support plate 39 for receipt of second cassette 11 through right access door 74, or vice versa. Placement of cassette 11 on support plate 38 or 39 actuates corresponding cassette detection sensors 46, which signals to controller 14 for verification of the presence of each cassette 11.

Next, linear actuator 41 translates inserted cassettes 11 to indicia reader 50 to scan the identifying indicia on each cassette 11 if present. If the operator has not yet specified the protocol, controller 14 may obtain it from the identifying indicia at this time. After any available information is obtained by indicia reader 50, linear actuator 41 translates cassettes 11 to position first probe 12 specified in the queue for engagement with probe hook 21.

Once positioned, probe detection sensor 46, or alternatively indicia reader 50, may sense whether selected probe 12 is present. If probe 12 is present, indicia reader 50 scans any identifying indicia on probe 12, if present. If no probe is present and depending on the operator-defined settings, controller 14 may either abort the queue or index the queue to the next probe specified. If the latter is chosen, controller 14 commands linear actuator 41 to position next probe 12 for engagement with probe hook 21, at which time the verification process begins anew.

When the presence of a selected probe 12 has been verified, controller 14 instructs sample receiving post 16 to move into chamber 26 and then vents chamber 26 to atmospheric pressure. Simultaneously, controller 14 may check upper limit sensor 31 to determine if probe hook 21 is appropriately positioned for engagement with probe 12. If probe hook 21 is not, motor 28 is actuated to translate probe hook 21 along rail 22 and screw 61 to the proper engagement position.

Upon vent completion, motor 33 is actuated to rotate rail 22 about the centerline of screw 61 by a predetermined angle, such as 45 degrees CCW. Slot 64 disposed along the length of rail 22 forces concerted rotation of lead nut 60, and thus probe hook 21 attached thereto, engaging probe hook 21 with groove 18 disposed on probe 12. Since cover plate 25 also is fixedly attached to rail 22, cover plate 25 is concurrently rotated by the same predetermined angle, opening chamber 26 and exposing receiving post 16. Receiving post 16 then is advanced to contact the underside of lower support plate 24 and align with present device 20a by interfacing with alignment pins 47.

Once probe hook 21 is engaged to selected probe 12, controller 14 actuates motor 28 to linearly translate probe hook 21 towards receiving post 16, thereby also translating probe 12. Translation ceases when probe 12 is inserted into receiving post 16. This position is indicated to controller 14 by the signal of lower limit sensor 32.

To disengage probe hook 21 from probe 12, motor 33 rotates rail 22 about the centerline of screw 61 an additional predetermined angle, such as 45 degrees CCW. Motor 28 then is actuated to reversibly translate probe hook 21 away from receiving post 16 so that probe hook 21 clears cover plate 25. Once probe hook 21 clears, motor 33 rotates rail 22 in a counter-direction, such as 90 degrees CW, thereby closing cover plate 25 and sealing vacuum chamber 26. Chamber 26 then may pump down to a predetermined operating pressure and receiving post 16 translates probe 12 to ion source chamber 51 of mass spectrometer 13 for analysis.

During analysis, linear actuator 41 may position cassette support plates 38 and 39 so that the operator may access either the left or right cassette positions. Typically, if mass spectrometer 13 is analyzing probe 12 that had been extracted from cassette 11 received within the left cassette position, linear actuator 41 will position right support plate 39 for exchange or receipt of new cassette 11 through right access door 74. Likewise, if mass spectrometer 13 is analyzing probe 12 extracted from cassette 11 received within the right cassette position, linear actuator 41 will position left support plate 38 for exchange or receipt of new cassette 11 through left access door 72. If new cassette 11 is inserted, controller 14 will indicate that the left and/or right cassette, as appropriate, was changed, and prompt the operator to specify a new protocol for new cassette 11 or register new cassette 11 from accompanying identifying indicia.

When analysis of present probe 12 within mass spectrometer 13 is complete, linear actuator 41 positions cassette 11, from which said probe 12 was originally extracted, with respect to chamber 26 so that it may receive analyzed probe 12. Receiving post 16, constraining analyzed probe 12, then is moved into chamber 26, which then is vented to atmospheric pressure. Next, motor 33 rotates rail 22 a predetermined angle, such as 90 degrees CCW, to open cover plate 25. The probe translation subassembly then translates probe hook 21 towards receiving post 16 until lower limit sensor 32 is actuated. Controller 14 then instructs motor 28 to cease actuation and instructs motor 33 to counter-rotate rail 22, such as by 45 degrees CW, to engage probe hook 21 to probe 12. Upon engagement, the probe translation subassembly linearly translates both probe hook 21 and probe 12 towards upper limit sensor 31 to reinsert probe 12 into its original cassette 11. When actuated, upper limit sensor 31 notifies controller 14 that reinsertion is complete and the probe rotation subassembly again counter-rotates probe hook 21 by an additional predetermined angle, such as 45 degrees CW, to disengage probe 12 and return probe hook 21 to its original position. Finally, controller 14 increments the queue and signals linear actuator 41 to position cassette(s) 11 for engagement of next probe 12 identified in the queue.

Once all the probes constrained in a first cassette 11 have been analyzed, controller 14 alerts the operator, and device 20a then may transfer probes 12 from a second cassette 11, if present, into mass spectrometer 13 for analysis. To alert the operator, a useful embodiment may comprise one or more indicator lights 78 (see FIG. 7), which may remain lit until cassette 11, constraining analyzed probes 12, is removed or exchanged. A useful embodiment may comprise one indicator light 78 for each cassette 11 that loading device 20a is configured to accept.

In the event that device 20a ceases to operate, device 20a may be manually actuated.

Referring to FIGS. 8A–B, an alternative embodiment of probe insertion assembly 55 is illustrated. Like assembly 55, probe insertion assembly 155 also comprises a probe hook 21 and probe translation and rotation subassemblies having the common elements of a rail 122 and a lead nut 160 slidably engaged thereto. Like the above-described coaxial embodiment, the probe translation subassembly further comprises a screw 161 having a centerline disposed parallel to rail 122, a motor 128, a first gear 129 fixedly attached to motor 128, and a second gear 130 that is fixedly attached to screw 161 and rotatably engaged to first gear 129. Screw 161 is rotatably engaged to lead nut 160 via an internally threaded through-bore 162. In operation, actuation of motor 128 rotates first gear 129, which rotates second gear 130 and screw 161 attached thereto. To constrain lead nut 160 from rotating with screw 161, and thereby limit movement of lead nut 160 to the Z axis when linear translation is desired, lead nut 160 further comprises an unthreaded through-bore 164 that slidably and rotatably engages rail 122. Thus, when motor 128 rotates screw 161, the presence of rail 122 within through-bore 164 prevents rotation of lead nut 160 with screw 161.

To rotate probe hook 21, the probe rotation subassembly further comprises a motor 133, a first gear 134 fixedly attached to motor 133, and a second gear 135 that is fixedly attached to rail 122 and is capable of being rotated about screw 161. When motor 133 is actuated, first gear 134 and second gear 135 are rotated in opposing directions. Rotation of second gear 135 rotates rail 122 attached thereto about the centerline of screw 161. Since rail 122 is rotatably engaged to lead nut 160 via through-bore 164, rotation of rail 122 forcibly rotates lead nut 160 in concert therewith. Like the above-described coaxial embodiment of probe insertion assembly 55, rail 122, lead nut 160, and second gear 135 rotate about the centerline of screw 161. Note that, unlike probe insertion assembly 55 which comprises a separate cover plate 25, second gear 135 of probe insertion assembly 155 serves as the cover plate. Like the cassette translation and probe insertion assemblies described herein, all linear and rotational positions may be tracked using one or more contact or non-contact type sensors, open loop control, rotary and/or linear encoders, resistance potentiometers, capacitive displacement sensors, or any other suitable means known in the art or combinations thereof.

Figure 9A:
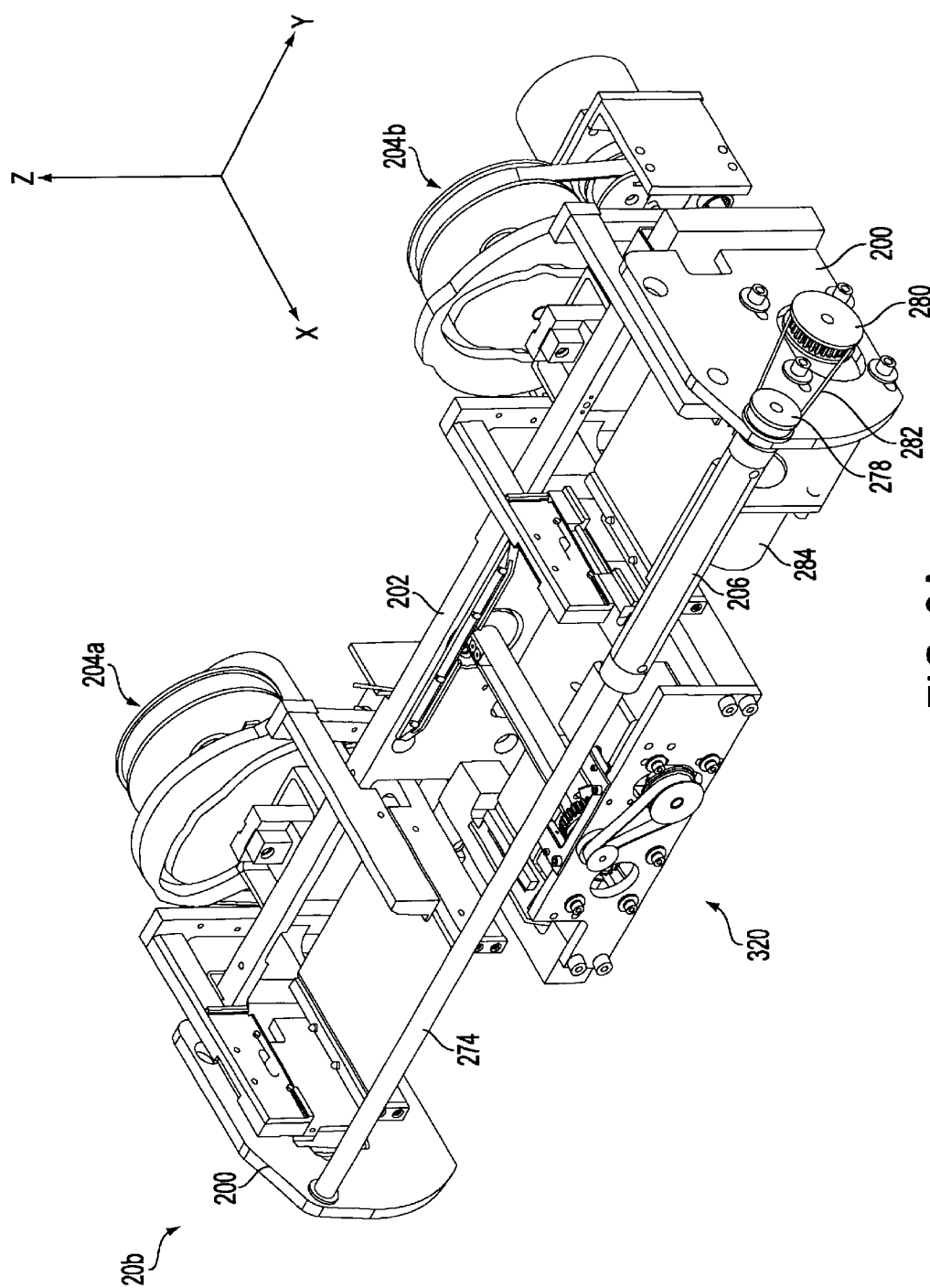
FIGS. 9A–B respectively are assembled and exploded perspective views of a second embodiment of the loading device of the present invention.
Figure 9B:
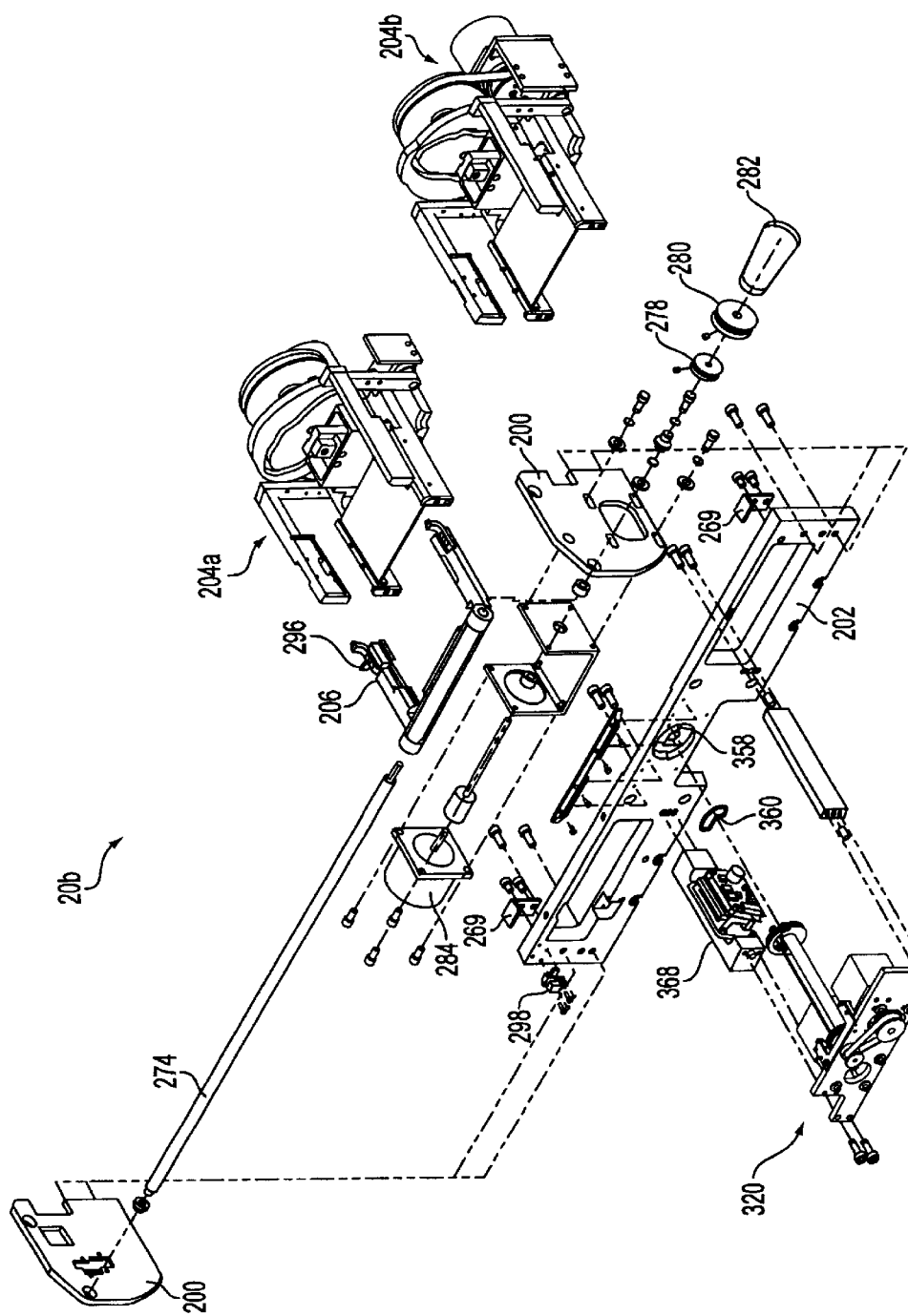

Referring now to FIGS. 9A–B, a second embodiment of loading device 20 is described. Similar to the above-described embodiment, loading device 20b comprises frame 200 having support plate 202 upon which components of a cassette transport assembly and probe insertion assembly may be mounted. Frame 200 may comprise a unitary structure upon which both cassette transport and probe insertion assemblies are mounted (as shown), or multiple structures, perhaps a separate structure for each assembly.

The cassette transport assembly linearly translates a single cassette 11 in the Y axis to position probes 12 constrained within the cassette for engagement with the probe insertion assembly. The probe insertion assembly engages and transfers individual probes initially constrained within the cassette between said cassette and receiving post 16 of analytical instrument 13. The cassette transport assembly includes cassette retention subassemblies 204 that each are configured to receive a plurality of cassettes 11, and shuttle 206 that individually transfers each cassette from cassette retention subassembly 204a to cassette retention subassembly 204b, pausing at intermediate positions therebetween to permit probes 12 initially constrained within each cassette to be transferred to analytical instrument 13 for analysis. Cassettes constraining a plurality of unanalyzed probes 12 may be loaded into cassette retention subassembly 204a to await individual transfer of each cassette to probe insertion assembly 320. Cassettes constraining a plurality of analyzed probes 12 may be transferred from probe insertion assembly 320 to cassette retention subassembly 204b to await removal of said cassettes from loading device 20b.

Figure 10A:
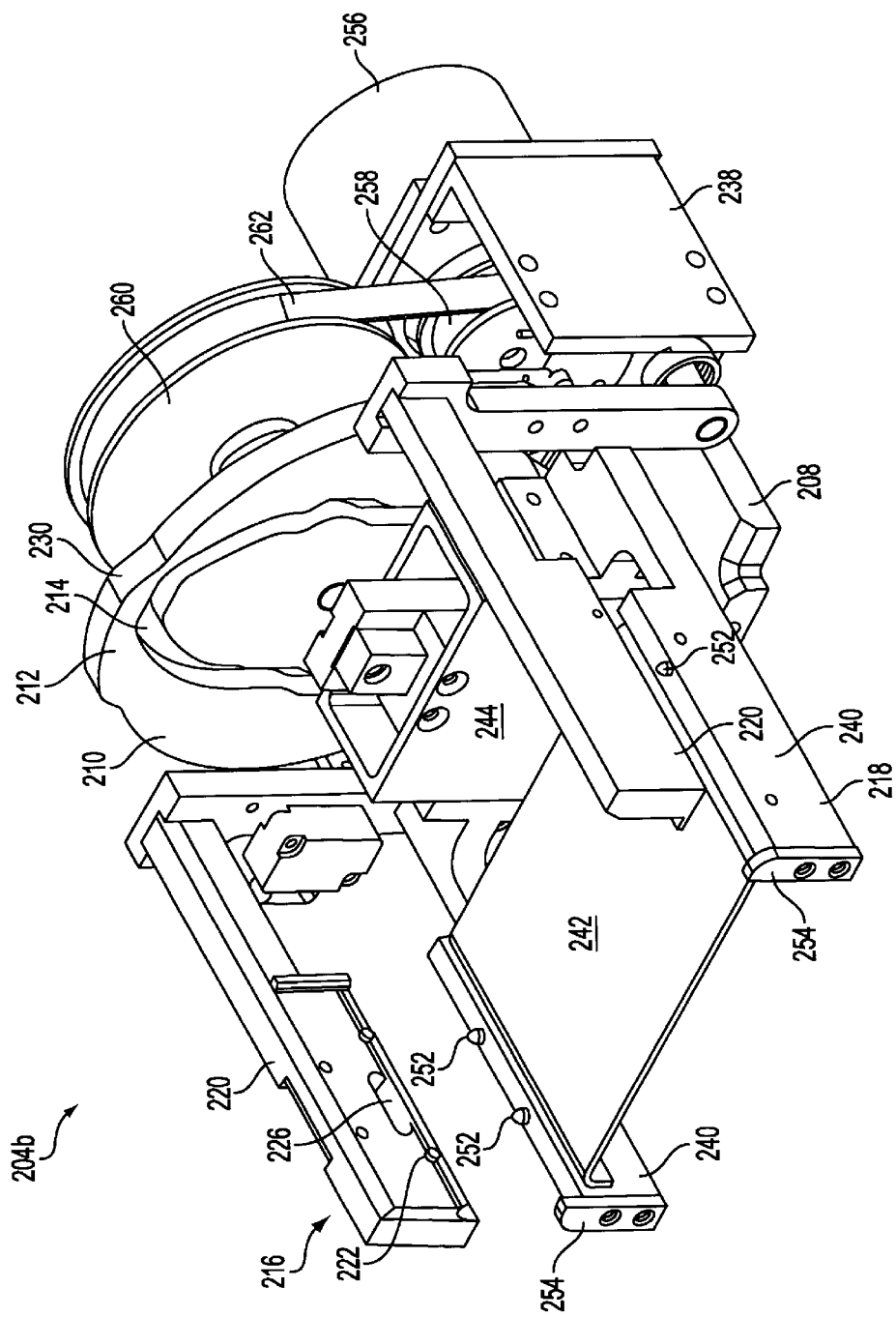
Figure 12A:
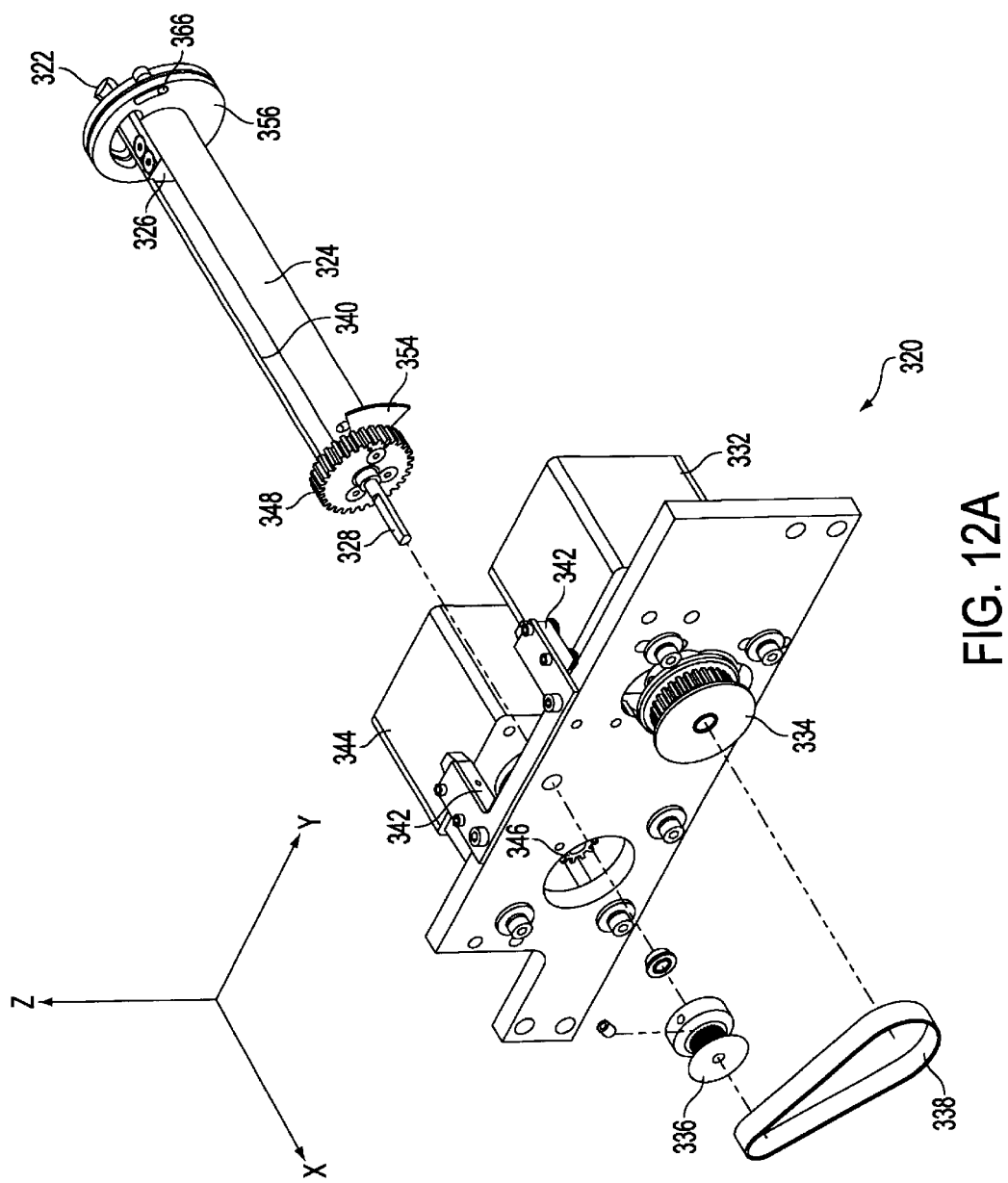
FIGS. 12A–B are exploded perspective views of a third embodiment of the probe insertion assembly of the present invention.
Figure 12B:
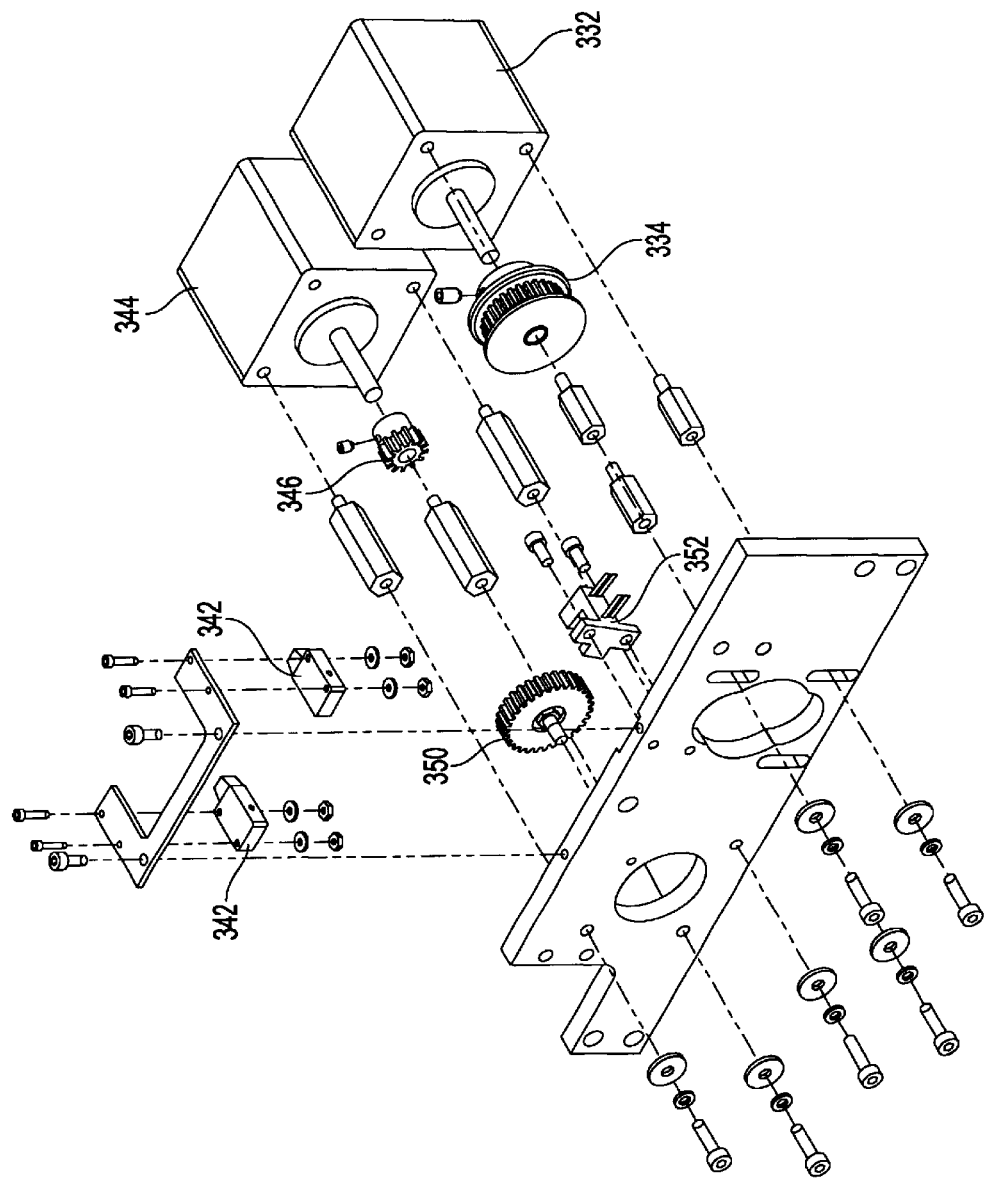

Referring now to FIGS. 10A–B, cassette retention subassembly 204b is described. Although cassette retention subassembly 204b is a mirror image of subassembly 204a in this embodiment, the subassemblies may be structured in a substantially similar manner. Either subassembly 204a or 204b may be used to transfer a cassette to or from shuttle 206, depending on the rotation of a cam component coupled to each subassembly. Accordingly, only subassembly 204b will be described in detail. Cassette retention subassembly 204b comprises a base 208 coupled to a cam 210 made from an irregularly shaped rigid disk having diametrically disposed lips 212, and irregularly shaped groove 214 milled or molded on one of its planar surfaces. Cam 210 is coupled to and actuates a support frame 216 and an elevator 218. Support frame 216 has a pair of support arms 220 that may accept a stack of cassettes comprising one or more cassettes therebetween. To retain the cassettes in support frame 216 and ensure that the cassettes are aligned with shuttle 206 and elevator 218, a plurality of cassette locator pins 222, configured to engage alignment slots in a lower surface of a cassette 11, is provided in support arms 220. Additional cassettes may be stacked on top of the bottom-most cassette by engaging similar alignment pins and holes in adjacent cassettes. The presence of a cassette may be detected by a cassette detection sensor 224 that interrogates the bottom-most cassette, if present, through hole 226 disposed through one of support arms 220. In a useful embodiment, cassette detection sensor 224 may comprise photoelectric switches, or other contact and non-contact sensors such as force/strain, pressure, or piezoelectric sensors.

Each support arm 220 is coupled to a cam follower 228 that couples support arm 220 to an outer edge 230 of cam 210. As illustrated in FIG. 10C, cam follower 228 illustratively may be made from a pin 232 having an annular bearing 234, e.g., a ball bearing. A torsion spring 236 is coupled to each support arm to bias cam follower 228 against cam 210, using spring retainer 238, e.g., a sheet of metal, to provide a counter-force. When cam followers 228 of support arms 220 engage lips 212 of cam 210, each support arm 220 is rotated away from the opposing support arm about each respective rotation axis 221, creating a span between the support arms that causes any retained cassettes to be released. Alternatively, rather than using torsion springs to bias the support arms against the outer edge of the cam, other structures may be employed to actuate rotation of each support arm upon rotation of the cam. For example, cam 210 may comprise a second additional groove milled or molded onto a planar surface of the cam, similar to groove 214. Cam followers 228 of support arms 220 may be disposed to engage the second groove, which may be configured to cause rotation of the support arms when the cam is rotated. This eliminates the need for torsion springs 236 and lips 212 of cam 210.

In a manner described in greater detail below, elevator 218 provides vertical support to a cassette when the cassette is transferred between shuttle 206 and cassette retention subassembly 204b. Elevator 218 incorporates elevator arms 240 attached to a platform 242 and elevator backbone 244, which in turn is attached to a linear bearing 246. In a useful embodiment, linear bearing 246 may comprise a cross-roller slide assembly, a linear ball bearing assembly or any other bearing that facilitates linear movement of elevator 218 with respect to base 208. Linear bearing 246 is fixed to a support post 248, which is attached to base 208. A cam follower 250 similar to cam followers 228 of support frame 216 also is coupled to backbone 244 and operably engaged to groove 214. Elevator 218 also has a plurality of pins 252 disposed on elevator arms 240 for engagement with alignment holes (not shown) disposed on a lower surface of each cassette 11, and shuttle cams 254 disposed on elevator arms 240 for engagement with shuttle 206 in a manner to be described in greater detail below.

Cam 210 is rotated by concerted action of motor 256, e.g., a stepper motor, first timing belt gear or pulley 258 attached to motor 256, second timing belt gear or pulley 260 attached to cam 210, and timing belt 262, which couples the first and second gears. When motor 256 rotates first gear 258, timing belt 262 forces rotation of second gear 260, thereby rotating cam 210. As would be apparent to one of ordinary skill in the art, cam 210 and any mechanism described herein may be actuated by any of a variety of commercially available motors or actuators, including DC, servo or pneumatic.

To track the angular orientation of cam 210, cassette retention subassembly 204b uses flags 264 affixed to cam 210, and home sensor 266 that is mounted to base 208 at a predefined home position. With respect to cassette retention subassemblies 204, the home position illustratively may be the position of cam 210 when support arms 220 are unrotated by lips 212 of the cam, and elevator 218 is situated in a non-elevated position. When in the home position, cam 210 has an angular orientation that disposes flags 264 to trigger home sensor 266, and thereby signal controller 14. Once cam 210 begins to rotate, controller 14 employs open loop control to count the number of steps or intervals from the home position. For example, if motor 256 is a stepper motor, the steps of the stepper motor may correlate to the angular displacement from the home position. When home sensor 266 is triggered by one of flags 264, controller 14 may recalibrate the intervals it has counted, thereby correcting any drift or error. The cassette retention subassembly also may use other means concurrently or instead of open loop control to track the angular orientation of cam 210, e.g., additional sensors disposed around the circumference of cam 210, resistive potentiometers, capacitive displacement sensors, or rotary encoders.

In operation, cam followers 228 of support frame 216 engage outer edge 230 of cam 210, and cam follower 250 of elevator 218 engages groove 214 of cam 210. When cam 210 is rotated from the home position, engagement of cam follower 250 with groove 214 causes elevator 218 to which cam follower 250 is engaged to ascend. Concurrently, torsion springs 236 urge cam followers 228 coupled to each support arm 220 of support frame 216 to engage outer edge 230 of cam 210. When cam followers 228 encounter lips 212, the lips deflect cam followers 228 in an outward direction against the bias of torsions springs 236. This in turn rotates support arms 220 to which cam followers 228 are coupled away from each other about their respective rotation axes 221. A practitioner skilled in the art will appreciate that the cam mechanism could be replaced with other mechanisms including individual motors to control and coordinate the motion of the elevator and support arms.

In FIGS. 11A–B, shuttle 206 of loading device 20b is illustrated. Shuttle 206 comprises cassette retention components that retain a single cassette, and are coupled to cassette translation components that facilitate translation thereof. In a useful embodiment, the cassette retention components include shuttle base 272 that serves as a support frame having shuttle support arms 294 configured to retain a single cassette therebetween. Rotatably coupled to each shuttle support arm 294 is a latch 300 that may impose a releasable constraining force on cassette 11. Latch axles 302 couple each latch 300 to one or more torsion springs 306 configured to bias latch 300 closed, and to a lever 304, which is actuable by shuttle cam 254 of cassette retention subassemblies 204 (see FIGS. 10A–B). When lever 304 engages with shuttle cam 254, the shuttle cam imparts an eccentric force on lever 304 that rotates latch axle 302 coupled thereto. This in turn rotates open latch 300 against the biasing force of torsion springs 306. If a cassette had been constrained in shuttle 206, engagement of shuttle cams 254 with levers 304 releases the constraining force imposed by latches 300. Any cassette initially constrained in shuttle 206 now may be removed therefrom, or a new cassette may be loaded into the shuttle. Each latch axle 302 is retained to shuttle base 272 by one or more axle retainers 308. Shuttle base 272 also may incorporate a plurality of cassette locator features 310. Cassette locator features 310 may include pins that are disposed to mate with a plurality of alignment holes (not shown) disposed in a lower surface of cassette 11, or other structures that facilitate alignment of a cassette 11 within shuttle based 272. For example, shuttle base 272 may act as a nest within which cassette 11 may be constrained. Additional guiding tabs or walls that urge the cassette into the proper position within shuttle 206 also may be employed.

In addition to the cassette retention components, shuttle 206 also is coupled to cassette translation components, including a drive nut 270 that is coupled to shuttle base 272 and configured to engage a screw 274. Illustrated in FIGS. 9A–B, screw 274 spans the longitudinal length between cassette retention subassemblies 204a and 204b, and incorporates threads that are configured to engage internally threaded through-bore 276 of drive nut 270. Screw 274 is attached rigidly to second timing belt gear or pulley 278, which is coupled to first timing belt gear or pulley 280 by timing belt 282. First gear 280 is rotated by motor 284, e.g., a stepper motor. Upon actuation of motor 284, first gear 280 rotates, causing timing belt 282 to force rotation of second gear 278. Since second gear 278 is attached to screw 274, the screw also begins to rotate. Depending on the direction that screw 274 is rotated, shuttle 206 is linearly translated between cassette retention subassemblies 204a and 204b. It should be apparent to one of ordinary skill in the art that additional linear actuation assemblies, such as linear actuator 41, a motor-driven pulley assembly, a telescoping arm assembly or any other linear actuators and guide systems known in the art, also may be used.

In a useful embodiment, to guide translation of shuttle 206 along screw 274, shuttle base 272 may be coupled to a guide nut 286 having a unthreaded through-bore 288, and one or more guide bearings 290 disposed to contact and ride a lateral surface of support plate 202 of the present loading device. Since guide bearings 290 are attached on cantilevered ends 292 of each shuttle support arm 294, contact between guide bearings 290 and support plate 202 provides vertical support to shuttle 206. Guide bearings 290 further function to prevent shuttle 206 from lifting during transfer of a cassette 11 between the shuttle and elevator 218. More specifically, guide bearings 290 are inserted between support base 202 and brackets 269, which are mounted to the support base (see FIG. 9B), when shuttle 206 translates to either one of cassette retention subassemblies 204a or 204b. While shuttle support arms 294 are cantilevered in this embodiment, one of ordinary skill in the art will recognize that a cross-bar also may be disposed across the shuttle support arms. Furthermore, in certain embodiments, guide nut 286 also may be internally threaded, and have an unthreaded exterior that permits it to be coupled to shuttle base 272 in a manner that coordinates engagement of the threads of guide nut 286 and lead nut 270 to lead screw 274. For example, the guide nut may be slidingly coupled and secured to base 272 at a position that coordinates engagement of the guide and drive nuts to the lead screw.

To help track the position of shuttle 206, and thereby cassette 11, during linear translation, a flag 296 is disposed protruding from an edge of shuttle 206. Flag 296 is positioned to trigger one or more home sensors 298 disposed at one or more positions along the longitudinal length of screw 274. In a useful embodiment, loading device 20b may employ open loop control to track the position of shuttle 206, in which controller 14 counts the number of steps or intervals from a predefined home position. The controller may be alerted to the home position by actuation of a home sensor 298, which illustratively may be disposed at either one of cassette retention subassemblies 204a or 204b. If a stepper motor is used, the steps of the stepper motor may be correlated to linear displacement of shuttle 206 from the home position. Other tracking means include using additional sensors disposed along the length of screw 274, resistive potentiometers, capacitive displacement sensors, or rotary encoders.

Referring now to FIGS. 12A–D, probe insertion assembly 320 is illustrated. Like probe insertion assembly 55 of loading device 20a, probe insertion assembly 320 also comprises a probe hook 322 to rotatably engage groove 18 of probe 12, a probe translation subassembly to linearly translate a probe 12 in the X axis between chamber 26 and a cassette 11, and a probe rotation subassembly to rotate probe hook 322 in a plane orthogonal to the X axis for engagement with or disengagement from probe 12. The probe translation and rotation subassemblies share common elements a rail 324 comprising a hollow shaft, and a lead nut 326 slidably coupled to the rail and upon which probe hook 322 is fixedly attached. The probe translation subassembly further comprises a screw 328 having a centerline disposed parallel to rail 324, and threads that engage threads disposed in an engagement portion 330, e.g., a through-bore, of lead nut 326. Together, screw 328, rail 324 and lead nut 326 comprise a screwrail that linearly actuates probe hook 322. It will be apparent to one of ordinary skill the art that, while FIGS. 12A–D illustrate an engagement portion that fully circumscribes screw 328, an engagement portion that engages only a fraction of the circumference of the screw, e.g., engagement portion 62 of loading device 20a, would not deviate from the present invention.

Screw 328 is rotated by concerted action of motor 332, first timing belt gear or pulley 334 attached to motor 332, second timing belt gear or pulley 336 attached to screw 328, and timing belt 338, which couples first gear 334 to second gear 336. When motor 332 rotates first gear 334, timing belt 338 forces rotation of second gear 336, which in turn rotates screw 328. To rotationally constrain lead nut 326 from rotating with screw 328, and thereby limit movement of lead nut 326 to the X axis when linear translation is desired, a slot 340 may be disposed along the longitudinal length of rail 324 to engage lead nut 326. The width of slot 340 is dimensioned to permit lead nut 326 to translate therealong but to restrict the lead nut from any rotational movement with respect thereto. Thus, when screw 328 is rotated, the walls of slot 340 serve as a track that establishes movement of lead nut 326 in the X axis. It should be apparent to one of ordinary skill in the art that additional linear actuation assemblies, such as linear actuator 41, a motor-driven pulley assembly, a telescoping arm assembly or any other linear actuators known in the art, also may be used.

To track the linear position of probe hook 322, the probe insertion subassembly employs open loop control in conjunction with home sensor 342 disposed at a predefined home position along the length of rail 324. When home sensor 342 is triggered, a signal is sent to controller 14 to notify the controller that probe hook 322 is disposed in the home position. When motor 332 is actuated to rotate screw 328, and thereby translate probe hook 322, controller 14 counts the steps or intervals from the home position, which correspond to the linear displacement of lead nut 326 from the home position. If the home position demarcates, for example, proper positioning of the probe hook for engagement or disengagement with a probe 12 fully constrained within a cassette 11, controller 14 would terminate actuation of lead nut 326 when the home sensor is triggered. If the home position demarcates, for example, a position that is a predetermined distance away from the position in which the probe hook is disposed for engagement or disengagement with a probe 12 fully constrained within a cassette 11, controller 14 would terminate actuation of lead nut 326 after the home sensor is triggered and the lead nut additionally is actuated that predetermined distance. In a useful embodiment, home sensor 342 may comprise a photoelectric sensor or other contact and non-contact sensors known in the art. The probe insertion assembly also may employ a plurality of sensors disposed along the length of rail 324, and in particular, at longitudinally opposing ends of the rail, to track the position of the probe hook. A rotary encoder also may be used in addition to or in replacement of open loop control.

In addition to rail 324 and lead nut 326, the probe rotation subassembly further comprises a motor 344, a first gear 346 attached to motor 344, a second gear 348 attached to rail 324, and an idler gear 350 rotatably engaged to both first and second gears 346 and 348. When motor 344 is actuated, first gear 346 rotates idler gear 350, which in turn rotates second gear 348. Since rail 324 is attached to second gear 348, rail 324 is rotated therewith. When the rail is rotated about the centerline of screw 328, slot 340 disposed along the screw provides a force against lead nut 326 that causes the lead nut, and thereby probe hook 322 attached thereto, to rotate. A useful embodiment may utilize the travel of lead nut 326 in the X axis during rotation of probe hook 322 to ensure successful engagement with groove 18 of probe 12, preventing the probe hook from "hanging up" on the edge of groove 18. Alternatively, the pitch of the threads on screw 328 may be designed so that travel of lead nut 326 in the X axis is negligible when rail 324 is rotated. It should be apparent to one of ordinary skill in the art that, similar to the other probe rotation subassemblies described herein, rotation also may be actuated by other mechanical assemblies, such as a motor-driven pulley assembly or any other rotary actuators known in the art.

To determine the angular position of probe hook 322, loading device 20b may comprise a plurality of position sensors actuated by a flag 354 coupled to rail 324 (as in the above-described embodiment), or employ open loop control in conjunction with a single home sensor 352 actuated by flag 354. Similar to the open loop control tracking methods described hereinabove, when flag 354 triggers home sensor 352, a signal is sent to controller 14 to notify the controller that rail 324, and thus probe hook 322, is in a predefined home position. Actuation of motor 344 to rotate rail 324 and probe hook 322 may be tracked by counting the steps or intervals from the home position, which correlate to the angular displacement of the probe hook from the home position.

In addition to probe hook 322, rail 324 also is coupled to a cover plate 356 that is disposed to cover a probe exchange port 358 (see FIG. 9B) substantially similar to probe exchange port 67 of FIGS. 5A–B. When the probe rotation subassembly is actuated, it concurrently rotates both cover plate 356 and probe hook 322 in their respective planes orthogonal to the X axis. Probe exchange port 358 is disposed through support plate 202, and provides a portal through which probe 12 may enter or exit probe-receiving chamber 26. Receiving post 16 of analytical instrument 13 may be aligned with probe exchange port 358 by interfacing with a plurality of alignment pins (not shown) disposed on the underside of support plate 202. In a useful embodiment, cover plate 356 serves as a valve to sustain a vacuum within chamber 26 of analytical instrument 13. For example, cover plate 356 may incorporate a plurality of layers 357 between which a plurality of ball bearings 362 are individually coupled to a plurality of ramps 364. When cover plate 356 is rotated to seal chamber 26 after an unanalyzed probe 12 has been loaded therein, a protrusion 259 contacts an edge of support plate 202 surrounding probe exchange port 358 (see FIG. 9B), thereby constraining rotation of layer 357c with respect to seal 360 (see FIG. 9B). Further rotation of the probe rotation subassembly causes ball bearings 362 to roll on their respective ramps 364, and differential rotation of the cover plate, rotating layers 357a–b and ball bearings 362 with respect to layer 357c and ramps 364 disposed thereon. As the ball bearings rotate on their respective ramps, the ball bearings linearly press cover plate 356 against seal 360 (see FIG. 9B). Advancement of ball bearings 362 on ramps 364 is limited by engagement of stop 366 with sector slot 367 disposed within the cover plate. Advantageously, this design prevents undesirable sliding contact between cover plate 356 and seal 360 since the cover plate is advanced in the −X direction only during the actual sealing operation and bottom-most layer 357c is constrained from rotation with respect to the seal when they are in contact.

In a useful embodiment, probe insertion assembly 320 also may comprise a probe detection sensor or an indicia reader 368 (see FIG. 9B) to detect the presence of probe 12 when constrained within cassette 11, and/or retrieve additional information from identifying indicia disposed to probes 12 and/or cassettes 11 as described hereinabove.

Figure 13A:
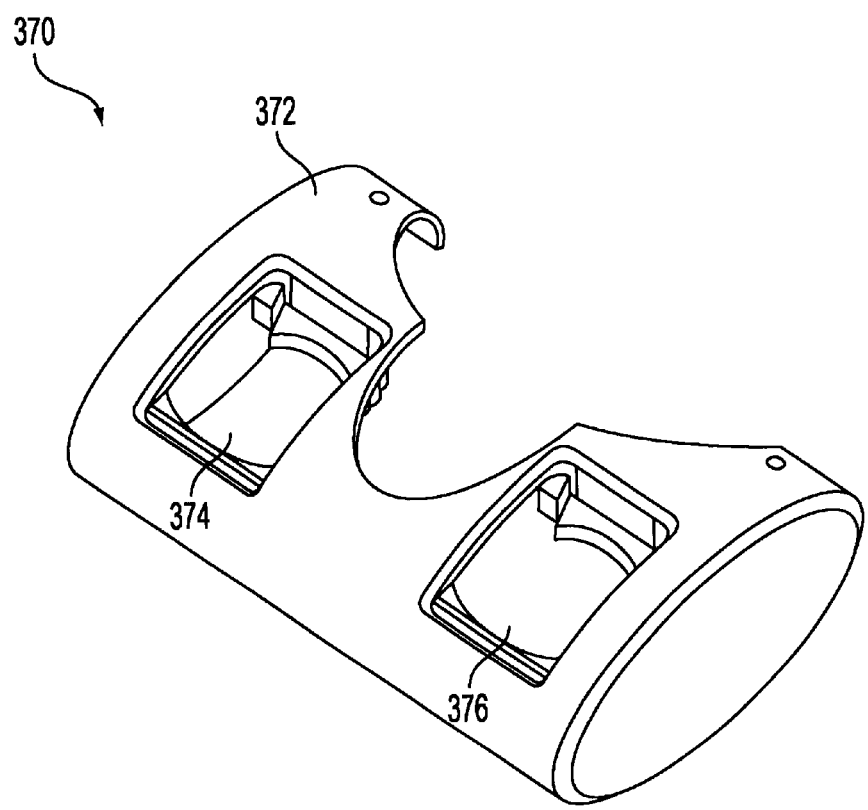
FIG. 13A is a perspective view a housing suitable for a second embodiment of the loading device of the present invention.

Referring now to FIG. 13A, in a useful embodiment, a housing 370 suitable for use with loading device 20b of the present invention is described. Housing 370 includes body 372, left access door 374 and right access door 376. Access doors 374 and 376 are coupled to body 372 and may be opened to access cassette retention subassemblies 204a and 204b. Should the operator want to load additional cassettes into cassette retention subassembly 204a, and/or unload cassettes from cassette retention subassembly 204b during mass spectrometric analysis of probes 12, or when loading device 20b and/or mass spectrometer 13 otherwise is idle, the operator may do so through access doors 374 and 376. Device 20b also may comprise a plurality of sensors similar to sensors 76 discussed with respect to FIG. 7 that communicate with controller 14 to detect that body 372 is in place and access doors 374 and 376 are closed prior to actuation of all or part of device 20b. If controller 14 determines that housing 370 is not properly located or that access doors 374 and 376 are not closed, controller 14 may inhibit actuation of device 20b until housing 370 is properly positioned and/or access doors 374 and 376 are closed. Advantageously, this protects the operator from moving parts. Alternatively, access doors 374 and 376 may be eliminated so that cassette retention subassemblies may be accessed at all times to load or unload cassettes from the device through openings 374 and 376 aligned with cassette retention subassemblies 204a and 204b, respectively.

Figure 13B:
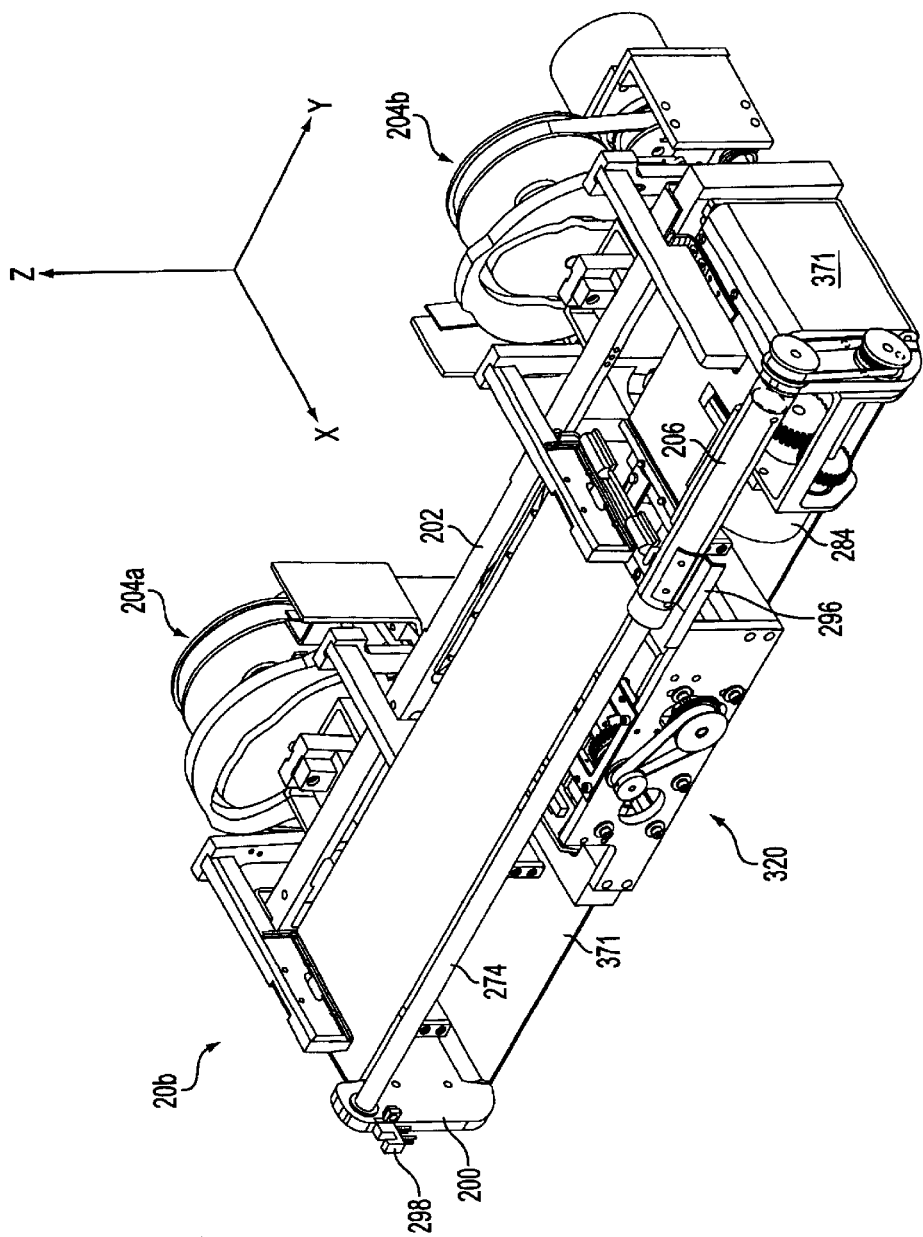
FIG. 13B is a perspective view of the loading device of the present invention having a safety feature that protects an operator from moving parts.

In a useful embodiment, the device of the present invention also may comprise other safety features to protect the operator from moving parts. For example, as illustrated in FIG. 13B, loading device 20b also may comprise a belt 371 made of a flexible material, coupled to shuttle 206 and slidably disposed surrounding device frame 200. When shuttle 206 is aligned with either one of cassette retention subassemblies 204a or 204b, belt 371 is disposed between elevator 218 and support frame 216 of the other cassette retention subassembly, thereby preventing access to the elevator but permitting cassettes to be loaded or unloaded from the support frame of that subassembly. When shuttle 206 begins to translate away from either one of the cassette retention subassemblies, the shuttle pulls the belt between elevator 218 and support frame 216 of both cassette retention subassemblies, thereby permitting access to both support frames 216, but preventing access to both elevators 218. Loading device 20b also may be equipped to alert controller 14 or shut down loading device 20b if the operator accidentally catches something, e.g., a finger, between belt 371 and support arm 220 of either cassette retention subassembly 204a or 204b. For example, if the operator reaches through doors or openings 374 or 376, and inadvertently catches, e.g., a finger between one of support arms 220 and belt 371 during translation of shuttle 206, deflection or rotation of that support arm past a predetermined deflection or rotation position triggers a sensor (not shown). The sensor then may alert controller 14 to cease translation of shuttle 206 and/or realign shuttle 206 with the cassette retention subassembly with which it initially was aligned, and/or the sensor signal may initiate an immediate emergency power shutdown, thereby permitting the operator to extract, e.g., his or her finger from the device. As would be apparent to one of ordinary skill in the art, device 20b slightly may be modified to accommodate unrestricted movement of belt 371 around device frame 200. For example, home sensor 298 may be relocated to a different position on frame 200, which may require relocation of flag 296 on shuttle 206 in certain embodiments. Additional gears also may be provided to couple motor 284 to lead screw 274 to actuate shuttle 206.

In a typical operation, the operator first disposes a stack of cassettes containing one or more cassettes 11 into cassette retention subassembly 204a through left access door 374. Placement of cassette(s) 11 within support frame 216 of cassette retention subassembly 204a triggers cassette detection sensor 224, which signals to controller 14 for verification of the presence of the bottom-most cassette. Next, controller 14 actuates motor 284 to move shuttle 206 into position above elevator 218 of cassette retention subassembly 204a. Linear actuation of the shuttle ceases either when flag 296 triggers home sensor 298 if the home sensor is disposed at cassette retention subassembly 204a, or when controller 14 counts the appropriate number of steps or intervals away from home sensor 298 if the home sensor is disposed elsewhere. Thereafter, motor 256 actuates rotation of cam 210 to raise elevator 218. As the elevator rises, engagement of shuttle cams 254 of the elevator with levers 304 of shuttle 206 opens cassette retention latches 300 in the manner described above for acceptance of an unanalyzed cassette 11. Elevator 218 continues to ascend until cassette locator pins 252 disposed on elevator support arms 240 engage alignment holes disposed in a lower surface of the bottom-most cassette constrained within support frame 216, transferring vertical support of the cassette stack to the elevator support arms.

As cam 210 continues to rotate, elevator 218 maintains approximately constant height. When cam follower 228 of each support arm 220 engage lips 212 of cam 210, each support arm is rotated about its rotation axis 221 away from the opposing support arm until the support arms clear cassettes 11 supported by elevator 218. As cam 210 continues to rotate, groove 214 of cam 210 causes elevator 218 to descend by the height of one cassette 11, and then maintains the elevator approximately at constant height. Lips 212 also are disengaged from cam followers 228 of support arms 220, permitting torsion springs 236 to bias the support arms back into its original position supporting the remaining cassettes within the original cassette stack. Elevator 218 proceeds to descend, supporting only the bottom-most cassette of the cassette stack.

When elevator 218 lowers the bottom-most cassette to the elevation of shuttle 206, alignment holes disposed on a lower surface of that cassette 11 engage cassette locator features 310 disposed on the shuttle. As cam 210 continues to rotate, elevator 218 continues to descend, transferring support of the bottom-most cassette to shuttle support arms 294. As elevator 218 descends below the elevation of shuttle 206, shuttle cams 254 coupled to elevator 218 disengages from levers 304, allowing torsion springs 306 to which latches 300 are coupled to bias the latches closed, thereby imposing a constraining force to bottom-most cassette 11 that secures the cassette to the shuttle. Rotation of cam 210, and thus descension of elevator 218, ceases when one of flags 264 coupled to cam 210 triggers home sensor 266.

Thereafter, controller 14 actuates motor 284 to rotate screw 274 and translate shuttle 206 constraining bottom-most cassette 11 to probe insertion assembly 320. Indicia reader 368 then may scan identifying indicia, if present, on the cassette. If the operator has not yet specified the protocol, controller 14 may obtain it from the identifying indicia at this time. After any available information is obtained by indicia reader 368, cassette 11 is translated to position first probe 12 specified in the queue for engagement with probe hook 322.

Once positioned, a probe detection sensor or indicia reader 368, may sense whether selected probe 12 is present. If probe 12 is present, indicia reader 368 scans any identifying indicia on probe 12, if present. If no probe is present and depending on the operator-defined settings, controller 14 may either abort the queue or index the queue to the next probe specified. If the latter is chosen, controller 14 commands the next probe to be positioned for engagement with probe hook 322, at which time the verification process begins anew.

When the presence of a selected probe 12 has been verified, controller 14 instructs sample receiving post 16 to move into chamber 26 and then vents chamber 26 to atmospheric pressure. Simultaneously, controller 14 may check if probe hook 322 appropriately is positioned for engagement with probe 12, for example, by communicating with home sensor 342. If probe hook 322 is not, motor 332 is actuated to translate probe hook 322 to the proper engagement position.

Upon vent completion, motor 344 is actuated to rotate rail 324 about the centerline of screw 328 by a predetermined angle, such as 45 degrees CCW. Slot 340 disposed along the length of rail 324 forces concerted rotation of lead nut 326, and thus probe hook 322 attached thereto, engaging probe hook 322 with groove 18 disposed on probe 12. Since cover plate 356 also is attached to rail 324, cover plate 356 concurrently is rotated by the same predetermined angle, opening chamber 26 and exposing receiving post 16. Receiving post 16 then is advanced to contact the underside of support plate 202 and align with present device 20b by interfacing with alignment pins disposed on the underside of the support plate.

Once probe hook 322 is engaged to selected probe 12, controller 14 actuates motor 332 to linearly translate probe hook 322 towards receiving post 16, thereby also translating probe 12. When controller 14 has counted a predetermined number of steps or intervals that inserts probe 12 into receiving post 16, translation ceases.

To disengage probe hook 322 from probe 12, motor 344 rotates rail 324 about the centerline of screw 328 an additional predetermined angle, such as 45 degrees CCW. Motor 332 then is actuated to reversibly translate probe hook 322 away from receiving post 16 so that probe hook 322 clears cover plate 356. Once probe hook 322 clears, motor 344 rotates rail 324 in a counter-direction, such as 90 degrees CW, thereby closing cover plate 356 and sealing vacuum chamber 26. Chamber 26 then may pump down to a predetermined operating pressure and receiving post 16 translates probe 12 to ion source chamber 51 of mass spectrometer 13 for analysis.

During analysis, the operator may load additional cassettes 11 into the stack of cassettes retained by cassette retention subassembly 204a, or unload analyzed cassettes from cassette retention subassembly 204b. If new cassette 11 is inserted, controller 14 will prompt the operator to specify a new protocol for new cassette 11 or register new cassette 11 from accompanying identifying indicia.

In the described embodiment, when analysis of present probe 12 within mass spectrometer 13 is complete, receiving post 16, constraining analyzed probe 12, is moved into probe receiving chamber 26, affecting a seal that permits probe receiving chamber 26 to be vented to atmospheric pressure while ion source chamber 51 is maintained under vacuum. Next, motor 344 rotates rail 324 a predetermined angle, such as 90 degrees CCW, to open cover plate 356. The probe translation subassembly then translates probe hook 322 towards receiving post 16 until it is positioned to engage probe 12 constrained therein. Controller 14 then instructs motor 332 to cease actuation and instructs motor 344 to counter-rotate rail 324, such as by 45 degrees CW, to engage probe hook 322 to probe 12. Upon engagement, the probe translation subassembly linearly translates both probe hook 322 and probe 12 towards, e.g., home sensor 342 to reinsert probe 12 into its original cassette 11, assuming the home sensor is disposed to demarcate the linear position at which probe 12 is fully constrained within cassette 11. When triggered, home sensor 342 notifies controller 14 that reinsertion is complete and the probe rotation subassembly again counter-rotates probe hook 322 by an additional predetermined angle, such as 45 degrees CW, to disengage probe 12 and return probe hook 322 to its original position. Finally, controller 14 increments the queue and actuates screw 274 to position cassette 11 for engagement of next probe 12 identified in the queue.

Once all the probes constrained in a first cassette 11 have been analyzed, controller 14 actuates screw 274 to translate shuttle 206 constraining the analyzed cassette to cassette retention subassembly 204b. The cassette is transferred from shuttle 206 to cassette retention subassembly 204b with the aid of elevator 218 of that cassette retention subassembly in a manner similar to but functionally reverse from, i.e., in the reverse order of, the transfer of the cassette from cassette retention subassembly 204a to shuttle 206.

Once the analyzed cassette has been transferred to cassette retention subassembly 204b, the empty shuttle may be translated back to cassette retention subassembly 204a to receive another cassette for analysis. Since cassette support frames 216 may receive more than one cassette 11, loading device 20b may be left unattended to analyze a multiplicity of cassettes without operator assistance or surveillance. Furthermore, the operator may choose to load one or more additional cassettes 11 into and/or remove one or more analyzed cassettes from loading device 20b without interrupting analysis of a probe 12. Cassettes loaded into device 20b are queued for analysis in the order the cassettes are loaded into device 20b. Similarly, cassettes constraining analyzed probes may be removed from device 20b in the order the cassettes originally were loaded into device 20b. Accordingly, the first unanalyzed cassette loaded into loading device 20b is the first analyzed cassette that may be unloaded from the device. Moreover, if a "high priority" cassette needs to be analyzed, unanalyzed cassettes constrained in cassette retention subassembly 204a may be removed, and the "high priority" cassette loaded into subassembly 204a for transfer to shuttle 206.

Furthermore, since cassette retention subassembly 204a structurally is substantially similar to cassette retention subassembly 204b, unanalyzed cassettes may be loaded into cassette retention subassembly 204b to await analysis and analyzed cassettes may be transferred into cassette retention subassembly 204a to await removal from the device. Alternatively, one of the cassette retention subassemblies may be dedicated to accepting "high priority" cassettes for immediate analysis without disturbing unanalyzed cassettes constrained within the other cassette retention subassembly that are awaiting analysis. Further alternatively, single cassettes may be loaded and retrieved from the same cassette retention subassembly, and shuttle 206 may be actuated to transfer cassettes from cassette retention subassemblies 204a and 204b to the probe insertion assembly in an alternating pattern. As would be apparent to one of ordinary skill in the art, since both cassette retention subassemblies may transfer cassettes to or from shuttle 206, thereby permitting acceptance of either unanalyzed or analyzed cassettes, additional algorithms may be employed. Indeed, controller 14 may be programmed to implement a multitude of user selectable algorithms for each analytical session.

In the event that device 20b ceases to operate, device 20b may be manually actuated.

Figure 14A:
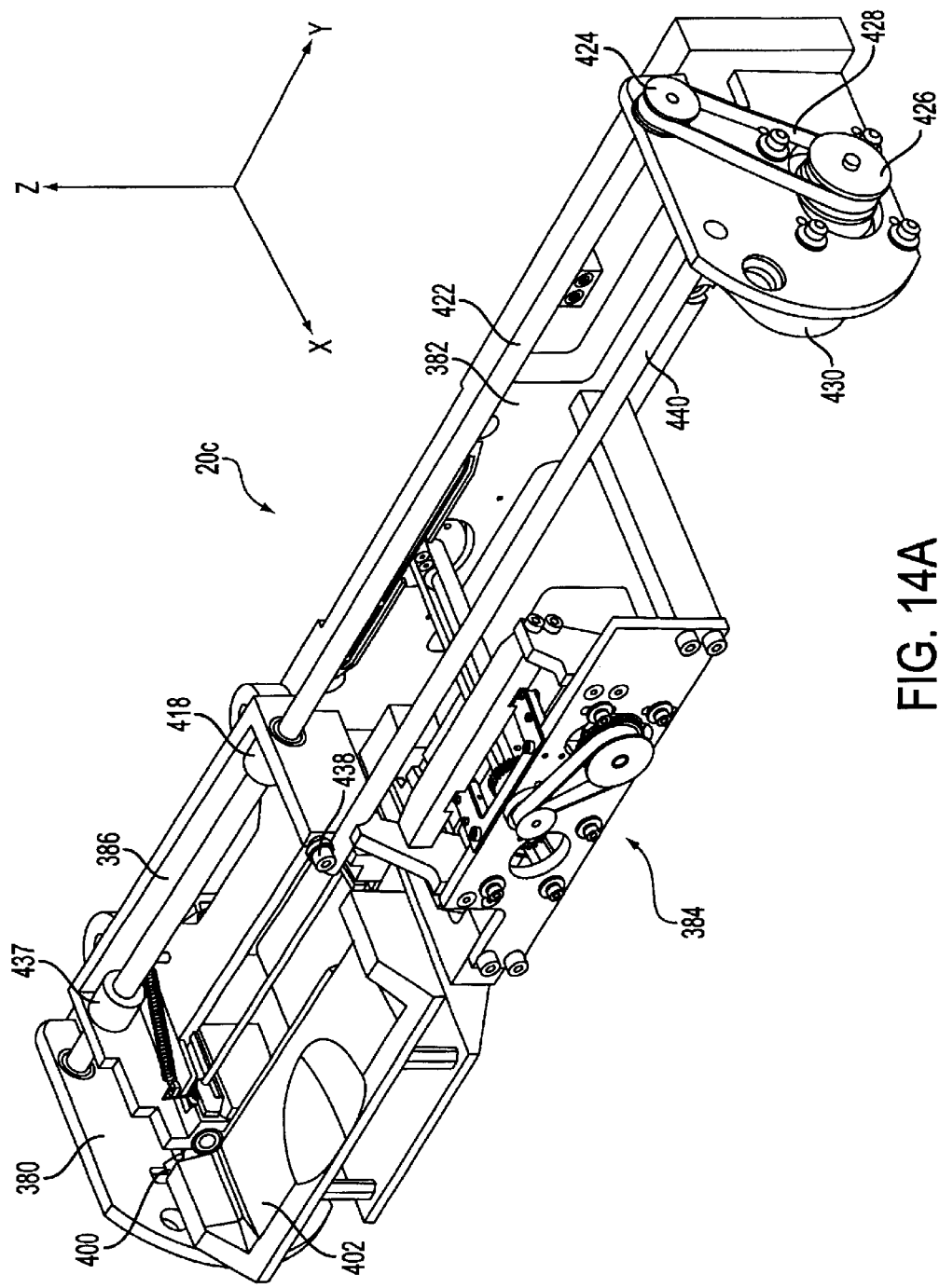
FIG. 14A is an assembled perspective view of a third embodiment of the loading device of the present invention.
Figure 14B:
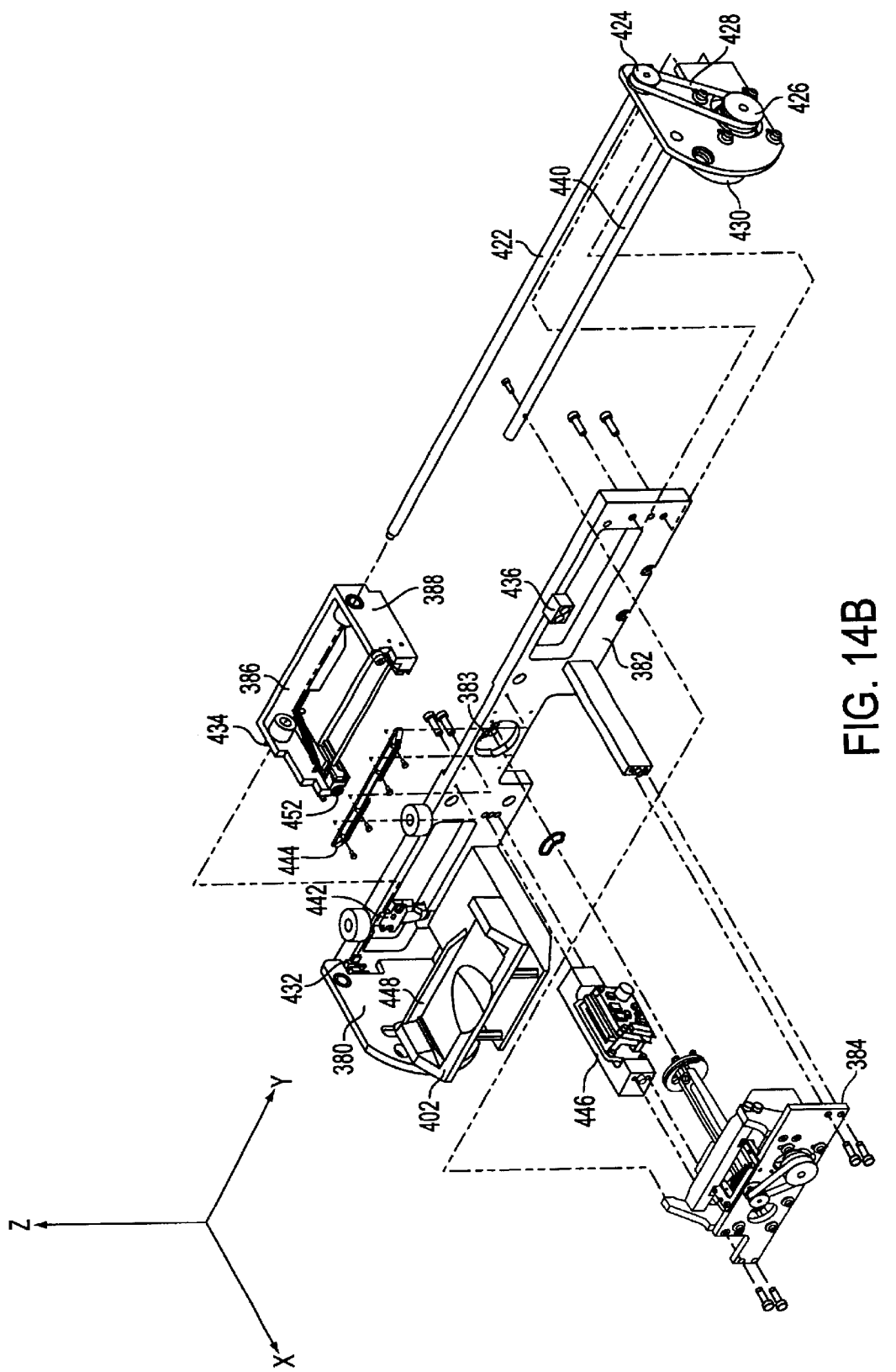
FIGS. 14B–C are exploded perspective views of the loading device of FIG. 13A.

Referring now to FIGS. 14A–B, a third embodiment of the loading device of the present invention is described. Similar to the above-described embodiments, loading device 20c comprises frame 380 having support plate 382 upon which components of a cassette transport assembly and a probe insertion assembly may be mounted. Like the frames of the above-described embodiments, frame 380 may comprise one or more structures, and support plate 382 includes a probe exchange port 383 through which a probe 12 may enter or exit probe-receiving chamber 26.

Figures 15A, 15B:
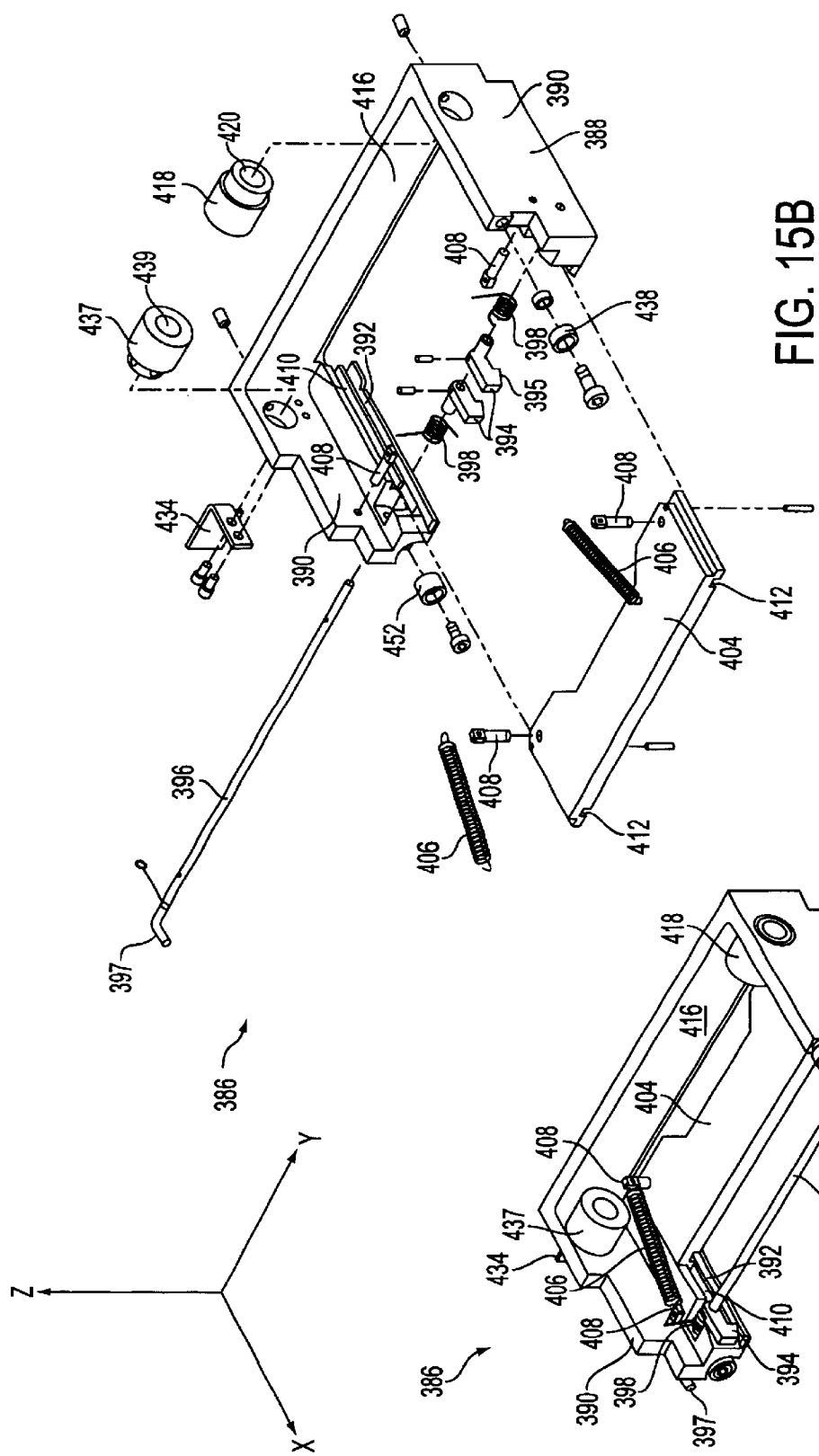
FIGS. 15A–B respectively are assembled and exploded perspective views of a shuttle of a cassette transport assembly of a third embodiment of the loading device of the present invention.

Loading device 20c of the present invention is configured to accept a single cassette 11 constraining a plurality of probes 12 and to transport that cassette to probe insertion assembly 384. The cassette transport assembly includes, inter alia, shuttle 386 configured to constrain and translate a single cassette. Illustrated in greater detail in FIGS. 15A–B, shuttle 386 includes cassette retention components comprising shuttle base 388 that serves as a support frame having shuttle support arms 390. On an inner lateral surface of each support arm 390 is disposed a first groove 392 within which a cassette 11 may be slidably constrained in the X axis and fully constrained in the Y and Z axes, and a second groove 410 disposed parallel to the first groove. To releasably constrain cassette 11 in the X direction, shuttle base 388 has one or more grips 394 coupled to a shaft 396 and coupled to one or more torsion springs 398. The torsion springs are configured to bias grips 394 closed, using shuttle base 388 to supply a counter-force. Accordingly, when a cassette 11 is fully seated in shuttle 386, grips 394 impose a releasable constraining force on the cassette that secures the cassette to the shuttle. Grips 394 may be opened against the spring tension in torsion springs 398 by applying an eccentric force to shaft 396 via handle 397. This may be accomplished by engagement of the handle with an actuation cam 400 that is pivotally coupled to frame 380.

Pursuant to one aspect of the present invention, shuttle 386 may comprise cassette retention components configured to release cassette 11 from the constraining force imposed by grips 394 and eject the cassette once shuttle 386 is positioned to receive a cassette for transfer, i.e., aligned with a cassette guide 402 (see FIGS. 14A–B) that aligns insertion of cassette into loading device 20c. This position hereinafter is referred to as the cassette load position. Shuttle 386 further includes cassette ejection slide 404 that is slidably disposed in the track formed by second grooves 410 and coupled to one or more extension springs 406. Anchors 408 secure one end of each extension spring 406 to cassette ejection slide 404 and the other end of each extension spring 406 to shuttle base 388. Disposed along the underside of cassette ejection slide 404 are channels 412 that partially extend into the depth of the cassette ejection slide.

In operation, when the operator inserts a cassette 11 into shuttle 386, the cassette contacts and slides along surfaces 395 of grips 394. Since surfaces 395 are inclined, the contact force between cassette 11 and grips 394 lifts the grips open against the bias of torsion springs 398. As the cassette is slid further into the track formed by first grooves 392, alignment pins 19 (see FIG. 1B) disposed on an upper surface of the cassette slide into channels 412. When the alignment pins reach the end of channels 412, additional force applied to the cassette in the −X direction pushes both the cassette and cassette ejection slide 404 in the −X direction against the spring force imposed by extension springs 406, until the cassette ejection slide abuts distal wall 416 of shuttle base 388. Torsion springs 398 then close grips 394, applying a constraining force to the cassette that fully secures the cassette in the shuttle. When shuttle 386 is translated back towards the cassette load position, i.e., in alignment with cassette guide 402, handle 397 of shaft 396 engages actuation cam 400, rotating grips 394 open and thereby allowing spring tension imparted by extension springs 406 to push cassette 11 out of the shuttle.

To facilitate translation of cassette 11 constrained within shuttle 386, a drive nut 418 similar to drive nut 270 of loading device 20b is coupled to shuttle base 388. Drive nut 418 has an internally threaded through-bore 420 configured to operably engage threads disposed on a screw. As illustrated in FIGS. 14A–B, screw 422 is attached to a second timing belt gear or pulley 424, which is coupled to first timing belt gear or pulley 426 via a timing belt 428. First gear 426 in turn is attached to a motor 430, e.g., a stepper motor, under the control of controller 14. When controller 14 actuates motor 430, rotation of first gear 426 actuates timing belt 428 to rotate second gear 424. Since the second gear is attached to screw 422, the screw also rotates, translating shuttle 386 along the screw in a linear direction dependent on the rotational direction of the screw. It should be apparent to one of ordinary skill in the art that additional linear actuation assemblies, such as linear actuator 41, a motor-driven pulley assembly, a telescoping arm assembly or any other linear actuators known in the art, also may be used.

To track the position of shuttle 386, and thus the position of a cassette constrained therein, controller 14 may employ open loop control, similar in manner to that described hereinabove, and a home sensor 432 disposed along the longitudinal length of screw 422. In a typical embodiment of loading device 20c, home sensor 432 is positioned to be triggered by a flag 434 mounted on shuttle 386 when the shuttle is positioned in the cassette load position. At this home position, flag 434 triggers home sensor 432, which signals to controller 14. When controller 14 actuates motor 430 to rotate screw 422, the controller counts the number of steps or intervals traveled by shuttle 386 from the home position to track the linear position of cassette 11 constrained within the shuttle. To prevent over-translation of shuttle 386, loading device 20c may include a stop 436 mounted on support plate 382.

Referring back to FIGS. 15A–B, shuttle 382 also may include components to guide linear translation of the shuttle. Shuttle 382 may incorporate a guide nut 437 similar to guide nut 286 of loading device 20b containing an unthreaded through-bore 439 configured to permit translation of screw 422 therethrough. Shuttle 382 also may incorporate a bearing 438, e.g., an annular ball bearing, that is disposed to travel on carriage support rail 440 (as shown in FIG. 14A). Not only does engagement between carriage support rail 440 and bearing 438 provide translational guidance, it also supplies additional structural support to shuttle support arms 390. As would be apparent to one of ordinary skill in the art, guide nut 286 also may be internally threaded, and have an unthreaded exterior that permits it to be coupled to shuttle base 272 in a manner that coordinates engagement of the threads of guide nut 286 and lead nut 270 to lead screw 274. For example, the guide nut may be slidingly coupled and secured to base 272 at a position that coordinates engagement of the guide and drive nuts to the lead screw.

Figure 14C:
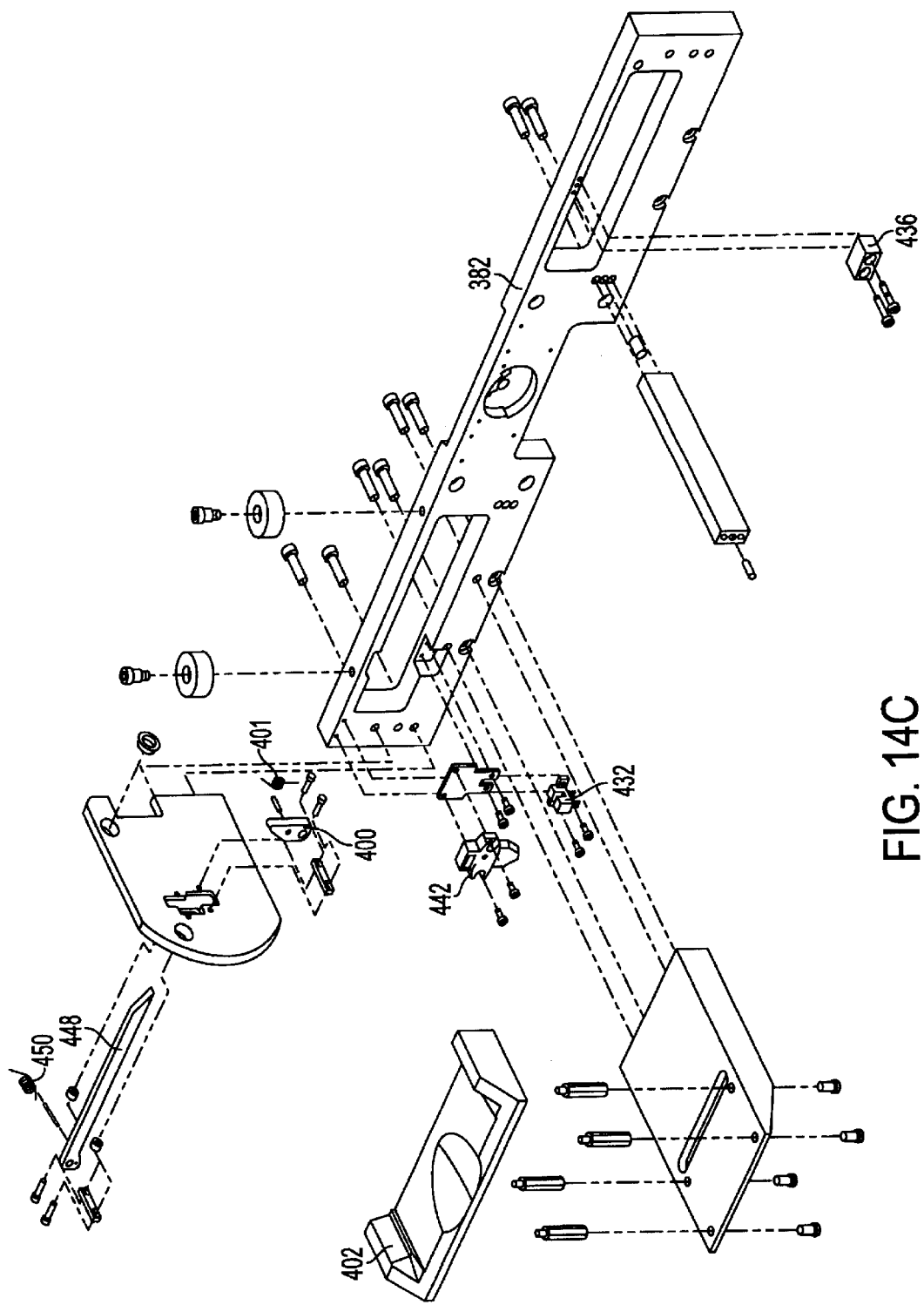

Pursuant to another aspect of the present invention, loading device 20c may be configured to prevent insertion of a cassette 11 into device 20c when shuttle 386 is not positioned to accept the cassette, i.e., not in the cassette load position. In particular, loading device 20c comprises gate 448 (see FIGS. 14B–C) pivotally coupled to frame 380. In the typical embodiment, a torsion spring 450 biases the gate to obstruct insertion of a cassette into loading device 20c when shuttle 386 is not aligned with cassette guide 402. When shuttle 386 is aligned with the cassette guide in the load position, gate actuation roller 452 coupled to shuttle 386 deflects gate 448 downward against the spring force of torsion spring 450, thereby permitting a cassette to be ejected from or loaded into shuttle 386. When shuttle 386 begins to translate away from the load position, cassette insertion initially is blocked by shuttle base 388, and then blocked by gate 448, which springs up into position when it is no longer deflected by gate actuation roller 452. Advantageously, not only does gate 448 prevent cassettes from being loaded into device 20c when shuttle 386 is not in the home position, it also acts as a safety feature, protecting the operator from moving parts.

Similar to above-described embodiments, loading device 20c further may comprise a cassette detection sensor 442 to detect the presence of a cassette constrained within shuttle 386 when the shuttle is positioned in the load position. The cassette detection sensor is mounted on frame 380 and coupled in electrical communication to controller 14. In a useful embodiment, cassette detection sensor 442 may include photoelectric sensors, or other contact or non-contact sensors known in the art. Also similar to above-described embodiments, loading device 20c further includes a cassette alignment strip 444 having a slot that spans the longitudinal length of the alignment strip. As shuttle 386 translates cassette 11 along screw 422, a complementary protrusion (not shown) on cassette 11 enters and rides along the slot, facilitating vertical alignment of the cassette in the Z axis. Loading device 20c also may incorporate a housing and safety features similar to that described with respect to FIGS. 13A–B.

The probe insertion assembly of loading device 20c may comprise any of the probe insertion assemblies described hereinabove in reference to FIGS. 5A–H, 6A–B, 8A–B, and 12A–D, including a probe detection sensor or an indicia reader 446 to detect the presence of a probe 12 constrained within a cassette 11 and/or retrieve information from indicia disposed on probe 12 or cassette 11.

Although useful illustrative embodiments of the present invention are described above, it will be apparent to one skilled in the art that various changes and modifications may be made without departing from the invention. It also will be apparent that the loading device and methods of the present invention are applicable to use in applications other than mass spectrometry, which was used in this description for illustrative purposes. It is intended in the appended claims to cover all such changes and modifications that fall within the true spirit and scope of the invention.

What is claimed is:

1. A device for automating transfer of a plurality of probes between a cassette within which the plurality of probes is initially constrained and an analytical instrument, the device comprising:
   a frame disposed external to a probe-receiving chamber integral to the analytical instrument;
   a cassette transport assembly attached to said frame, said cassette transport assembly having:
      (a) cassette retention means to receive the cassette, and
      (b) cassette translation means to linearly translate the cassette in a first axis to a defined insertion/removal position that aligns the cassette with respect to the probe-receiving chamber so that a select probe from the plurality of probes may be translated therebetween; and
   a probe insertion assembly attached to said frame, the probe insertion assembly having:
      (a) engagement means to rotatably engage one of the plurality of probes,
      (b) rotation means to rotate the engagement means, and
      (c) probe translation means to translate the engagement means in a second axis orthogonal to said first axis, wherein translation of one of the plurality of probes along said second axis translates that probe between the cassette and probe-receiving chamber.

2. The device of claim 1, wherein said rotation means and said probe translation means comprise common structures.

3. The device of claim 2, wherein the common structures comprise a rail and a carriage, wherein said carriage is engaged to said rail so that said carriage is capable of being translated therealong and rotated therewith.

4. The device of claim 3, wherein said rotation means further comprises a motor coupled to said rail, wherein actuation of said motor rotates said rail, and consequently rotates said carriage.

5. The device of claim 3, wherein said engagement means is disposed on said carriage so that said engagement means translates and rotates with said carriage, and engages or disengages one of the plurality of probes upon rotation of said carriage.

6. The device of claim 3, wherein said probe translation means further comprises a rotatable screw having a centerline disposed parallel to said rail and rotatably engaged to said carriage.

7. The device of claim 6, wherein engagement of said carriage to said rail constrains said carriage from rotating with said screw when linear translation of said carriage is desired.

8. The device of claim 7, wherein said rail comprises a longitudinal slot, said carriage disposed to engage said slot.

9. The device of claim 6, wherein said probe translation means further comprises a motor coupled to said screw to actuate rotation of said screw.

10. The device of claim 1, wherein said probe insertion assembly further comprises a cover plate through which the engaged probe is translated into or out of the analytical instrument, the cover plate disposed to cover the chamber of the analytical instrument.

11. The device of claim 10, wherein said cover plate is coupled to said rotation means so that actuation of said rotation means concurrently rotates both said cover plate and said engagement means.

12. The device of claim 10, wherein said cover plate is configured to sealingly cover the chamber to sustain a vacuum therein.

13. The device of claim 1, wherein said probe insertion assembly further comprises at least one sensor to track the angular position of said engagement means.

14. The device of claim 1, wherein said probe insertion assembly further comprises a rotary encoder to track the linear position of said engagement means.

15. The device of claim 1, wherein said probe insertion assembly further comprises at least one sensor to track the linear position of said engagement means.

16. The device of claim 1, wherein the linear position of said engagement means is tracked via open loop control.

17. The device of claim 1, wherein the angular position of said engagement means is tracked via open loop control.

18. The device of claim 1, wherein said engagement means comprises mechanical engagement means to engage one of the plurality of probes.

19. The device of claim 1, wherein said engagement means comprises a protuberance that engages a slot in one of the plurality of probes.

20. The device of claim 1, wherein said engagement means rotates in a plane orthogonal to said second axis.

21. The device of claim 1, wherein said device is configured to accept a plurality of cassettes each removably constraining a plurality of probes.

22. The device of claim 21, wherein said device is configured to permit each one of the plurality of cassettes to be independently interchanged with a separate cassette removably constraining a separate plurality of probes during analysis.

23. The device of claim 1, further comprising at least one sensor to sense the presence of the cassette.

24. The device of claim 23, wherein the sensor is a photoelectric sensor.

25. The device of claim 1, further comprising a controller that accepts digital information, comprising a protocol that specifies the order in which each probe of the plurality of probes should be transferred into the analytical instrument for analysis, the controller configured to control said cassette transport assembly and said probe insertion assembly responsive to the digital information.

26. The device of claim 25, further comprising a spare probe slot integral with said cassette transport assembly, wherein said spare probe slot may accept at least one spare probe.

27. The device of claim 26, wherein said controller is configured to interrupt the protocol responsive to acceptance of a single unanalyzed probe within said spare probe slot so that the single unanalyzed probe may be transferred to the analytical instrument for analysis prior to transferring the next probe specified in the protocol.

28. The device of claim 26, wherein said controller is configured to actuate said device to transfer one of the plurality of probes from the analytical instrument to said spare probe slot responsive to the removal of the cassette from said device prior to completion of the analysis of the one probe.

29. The device of claim 26, wherein said controller is configured to actuate said device to transfer one of the plurality of probes from the analytical instrument to said spare probe slot responsive to unsuccessful attempts by said device to load one of the plurality of probes into the analytical instrument.

30. The device of claim 26, wherein said controller is configured to direct said cassette transport assembly to position said spare probe slot with respect to the chamber to permit the spare probe to be inserted into or removed from said spare probe slot.

31. The device of claim 1, further comprising an indicia reader.

32. The device of claim 31, wherein said indicia reader is configured to detect the presence of the probe to be translated.

33. The device of claim 1, wherein said cassette translation means comprises a linear actuator to translate the cassette in said first axis.

34. The device of claim 33, further comprising one or more sensors disposed along a longitudinal length of said linear actuator to track the position of the cassette.

35. The device of claim 34, wherein said one or more sensors comprises two sensors disposed at longitudinally opposite ends of said linear actuator to indicate the ends of travel.

36. The device of claim 1, further comprising a linear encoder to track the position of the cassette.

37. The device of claim 1, wherein the position of the cassette is tracked via open loop control.

38. The device of claim 1, wherein said cassette retention means comprises a cassette support plate to receive the cassette and at least one pin to releasably engage the cassette to said support plate.

39. The device of claim 1, wherein said cassette retention means comprises at least one support frame configured for engagement with the cassette.

40. The device of claim 39, wherein said at least one support frame is coupled to said cassette translation means so that said cassette retention means is translated with the cassette.

41. The device of claim 1, wherein said cassette retention means imposes a constraining force on the cassette that releasably constrains the cassette.

42. The device of claim 41, wherein said cassette transport assembly releases said constraining force.

43. The device of claim 41, wherein said cassette retention means comprises one or more springs biased to impose said constraining force on the cassette.

44. The device of claim 1, further comprising a gate that blocks the cassette from being loaded into said device when said cassette retention means is not positioned to accept the cassette.

45. The device of claim 44, wherein said gate opens when said cassette retention means is positioned to accept the cassette.

46. The device of claim 39, wherein said at least one support frame comprises first and second support frames.

47. The device of claim 46, wherein each one of said first and second support frames is configured to receive a plurality of cassettes.

48. The device of claim 46, wherein said cassette translation means transports the cassette between said first and second support frames.

49. The device of claim 39, wherein said cassette transport assembly further comprises at least one elevator.

50. The device of claim 49, wherein said cassette transport assembly further comprises a cam coupled to said at least one elevator and said at least one support frame.

51. The device of claim 50, wherein actuation of said cam actuates said at least one elevator and said at least one support frame.

52. The device of claim 39, wherein said at least one support frame comprises a plurality of rotatable supports.

53. The device of claim 1, wherein said device is configured so that it may be manually actuated.

54. The device of claim 1, further comprising a removable housing to encompass said frame, cassette transport assembly, and probe insertion assembly.

55. The device of claim 54, further comprising at least one door disposed on said housing to facilitate insertion and/or removal of the cassette.

56. The device of claim 55, further comprising at least one sensor to detect proper placement of said housing and closure of said at least one door before allowing actuation of said device.

57. A system for automating transfer of a plurality of probes to an analytical instrument, the system comprising:
 a cassette to removably constrain the plurality of probes in a fixed spatial relationship;
 a loader to transfer the plurality of probes between said cassette and the analytical instrument, said loader having:
  a frame disposed external to a probe-receiving chamber integral to the analytical instrument;
  a cassette transport assembly attached to said frame, said cassette transport assembly having:
   (a) cassette retention means to receive the cassette, and
   (b) cassette translation means to linearly translate the cassette in a first axis to a defined insertion/removal position that aligns the cassette with respect to the probe-receiving chamber so that a select probe from the plurality of probes may be translated therebetween; and
  a probe insertion assembly attached to said frame, the probe insertion assembly having:
   (a) engagement means to rotatably engage one of the plurality of probes,
   (b) rotation means to rotate the engagement means, and
   (c) probe translation means to translate the engagement means in a second axis orthogonal to said first axis, wherein translation of one of the plurality of probes along said second axis translates that probe between the cassette and probe-receiving chamber.

58. A kit for automating transfer of a plurality of probes to an analytical instrument, the kit comprising:
 a cassette to removably constrain the plurality of probes in a fixed spatial relationship;
 a loader to transfer the plurality of probes between said cassette and the analytical instrument, said loader having:
  a frame disposed external to a probe-receiving chamber integral to the analytical instrument;
  a cassette transport assembly attached to said frame, said cassette transport assembly having:
   (a) cassette retention means to receive the cassette, and
   (b) cassette translation means to linearly translate the cassette in a first axis to a defined insertion/removal position that aligns the cassette with respect to the probe-receiving chamber so that a select probe from the plurality of probes may be translated therebetween; and
  a probe insertion assembly attached to said frame, the probe insertion assembly having:
   (a) engagement means to rotatably engage one of the plurality of probes,
   (b) rotation means to rotate the engagement means, and
   (c) probe translation means to translate the engagement means in a second axis orthogonal to said first axis, wherein translation of one of the plurality of probes along said second axis translates that probe between the cassette and probe-receiving chamber.

59. A kit for automating transfer of a plurality of samples into an analytical instrument, the kit comprising:
 a plurality of probes to accept the samples at discretely interrogatable locations;
 a cassette to removably constrain the plurality of probes in a fixed spatial relationship;
 a loader to transfer said plurality of probes between said cassette and the analytical instrument, said loader having:
  a frame disposed external to a probe-receiving chamber integral to the analytical instrument;
  a cassette transport assembly attached to said frame, said cassette transport assembly having:
   (a) cassette retention means to receive the cassette, and
   (b) cassette translation means to linearly translate the cassette in a first axis to a defined insertion/removal position that aligns the cassette with respect to the probe-receiving chamber so that a select probe from the plurality of probes may be translated therebetween; and
  a probe insertion assembly attached to said frame, the probe insertion assembly having:
   (a) engagement means to rotatably engage one of the plurality of probes,
   (b) rotation means to rotate the engagement means, and
   (c) probe translation means to translate the engagement means in a second axis orthogonal to said first axis, wherein translation of one of the plurality of probes along said second axis translates that probe between the cassette and probe-receiving chamber.

60. A method for automating transfer of a plurality of probes between a cassette within which the plurality of probes are initially constrained and an analytical instrument, the method comprising:
 (a) loading the cassette into the cassette retention means of claim 1;
 (b) actuating said cassette translation means to translate the cassette to one of the insertion/removal positions;
 (c) actuating said rotation means to rotatably engage said engagement means with one of the plurality of probes;
 (d) actuating said probe translation means to translate said engagement means in said second axis, thereby translating one of the plurality of probes into the analytical instrument for analysis; and
 (e) actuating said probe insertion assembly to rotatably engage and translate one of the plurality of probes out of the analytical instrument upon completion of the analysis thereof.

61. The method of claim 60, wherein the loading step further comprises loading a plurality of cassettes each constraining a plurality of probes into said device.

62. The method of claim 60, further comprising exchanging the cassette for a separate cassette constraining a plurality of probes.

63. The method of claim 62, wherein the exchanging occurs during analysis of one of the plurality of probes.

64. The method of claim 60, wherein the cassette retention means further comprises a spare probe slot that may accept a single probe; and the method further comprising actuating said device to insert the single probe into said spare probe slot.

65. The method of claim 60, further comprising reiterating steps (b) to (e) to analyze all probes constrained within the cassette.

66. The method of claim 60, wherein the cassette retention means comprises a transitory support frame coupled to said cassette translation means and a first non-transitory support frame; and wherein the loading step comprises:

loading the cassette into said first non-transitory support frame; and actuating said cassette transport assembly to transfer the cassette from said first non-transitory support frame to said transitory support frame.

67. The method of claim 66, wherein said cassette retention means further comprises a second non-transitory support frame; the method further comprising:

actuating said cassette translation means to translate the cassette from one of the insertion/removal positions to said second non-transitory support frame; and actuating said cassette transport assembly to transfer the cassette from said transitory support frame to said second non-transitory support frame.

68. A device for automating transfer of a plurality of probes between a cassette within which the plurality of probes is initially constrained and an analytical instrument, the device comprising:

a frame disposed external to a probe-receiving chamber integral to the analytical instrument;

a cassette transport assembly attached to said frame, said cassette transport assembly having:
 (a) a cassette support frame configured to receive the cassette, and
 (b) a cassette linear actuator subassembly configured to linearly translate the cassette in a first axis to a defined insertion/removal position that aligns the cassette with respect to the probe-receiving chamber so that a select probe from the plurality of probes may be translated therebetween; and a probe insertion assembly attached to said frame, the probe insertion assembly having:
 (a) an engagement piece configured to rotatably engage one of the plurality of probes,
 (b) a rotary actuator subassembly configured to rotate the engagement element, and
 (c) a probe linear actuator subassembly configured to translate the engagement element in a second axis orthogonal to said first axis, wherein translation of one of the plurality of probes along said second axis translates that probe between the cassette and probe-receiving chamber.

* * * * *